(12) United States Patent
Paris et al.

(10) Patent No.: US 7,482,123 B2
(45) Date of Patent: Jan. 27, 2009

(54) BIOMARKERS FOR PROSTATE CANCER METASTASIS

(75) Inventors: Pamela L. Paris, San Francisco, CA (US); Colin C. Collins, San Rafael, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/267,461

(22) Filed: Nov. 4, 2005

(65) Prior Publication Data

US 2006/0110759 A1    May 25, 2006

Related U.S. Application Data

(60) Provisional application No. 60/625,399, filed on Nov. 5, 2004.

(51) Int. Cl.
  *C12Q 1/68*  (2006.01)
  *C07H 21/04*  (2006.01)
(52) U.S. Cl. .......................... 435/6; 536/23.1; 536/24.3
(58) Field of Classification Search .................. None
  See application file for complete search history.

(56) References Cited

OTHER PUBLICATIONS

Paris, Pamela et al. Whole genome scanning identifies genotypes assocaited with recurrence and metastasis in prostate tumors. May 2004. Human Molecular Genetetics. vol. 13 No. 13 pp. 1303-1313.*

Paris, Pamela L. et al.; "Whole genome scanning identifies genotypes associated with recurrence and metastasis in prostate tumors"; 2004, *Human Molecular Genetics*, vol. 13, No. 13, pp. 1303-1313.

Van Dekken, Herman et al.; "Evaluation of Genetic Patterns in Different Tumor Areas of Intermediate-Grade Prostatic Adenocarcinomas by High-Resolution Genomic Array Analysis"; 2004, *Genes, Chromosomes & Cancer*, vol. 39, pp. 249-256.

Wang, S. et al.; "Prostate-specific deletion of the murine Pten tumor suppressor gene leads to metastatic prostate cancer"; 2003, *Cancer Cell*, vol. 4, No. 3, pp. 209-221.

* cited by examiner

*Primary Examiner*—Carla Myers
*Assistant Examiner*—Amanda Shaw
(74) *Attorney, Agent, or Firm*—Townsend and Townsend and Crew LLP

(57) ABSTRACT

The present invention provides genomic markers for determining the predisposition of prostate cancer to become metastasized.

3 Claims, 3 Drawing Sheets

SEQUENCE LISTING

<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:CUB and
      Sushi multiple domains 1 (CSMD1) TaqMan forward primer

<400> SEQUENCE: 1
tttccagatt tttatccaaa ctctctaa                                          28

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:CUB and
      Sushi multiple domains 1 (CSMD1) TaqMan probe
<220> FEATURE:
<221> NAME/KEY: modified_base
<222> LOCATION: (1)
<223> OTHER INFORMATION: n = c modifies by FAM
<220> FEATURE:
<221> NAME/KEY: modified_base
<222> LOCATION: (27)
<223> OTHER INFORMATION: n = g modified by black hole quencher 1 (BHQ1)

<400> SEQUENCE: 2
nacgtggacc attgaagtgt ctcatgn                                           27

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:CUB and
      Sushi multiple domains 1 (CSMD1) TaqMan reverse primer -continued

```
<400> SEQUENCE: 3
gtgtgaaaga tcatttgaac tcctttt                                              26
```

US 7,482,123 B2

BIOMARKERS FOR PROSTATE CANCER METASTASIS

CROSS REFERENCE TO RELATED PATENT APPLICATIONS

The present patent application claims benefit of priority to U.S. Provisional Patent Application No. 60/625,399, filed on Nov. 5, 2004, which is incorporated by reference for all purposes.

STATEMENT AS TO RIGHTS TO INVENTIONS MADE UNDER FEDERALLY SPONSORED RESEARCH OR DEVELOPMENT

This invention was made with Government support under Grant No. CA89520, awarded by the National Institutes of Health. The Government has certain rights in this invention.

BACKGROUND OF THE INVENTION

Prostate cancer is the most commonly diagnosed non-cutaneous neoplasm among males in Western countries and is estimated to result in 28,900 deaths this year in the U.S. alone. The advent of widespread PSA screening has resulted in increased detection of prostate cancer at earlier stages. A persistent and recalcitrant problem is that men with similar stage tumors often exhibit markedly different clinical outcomes following therapy, i.e. surgery or radiation. Early detection combined with slowly progressing tumors means a significant subset of men may be candidates for watchful waiting or active surveillance rather than treatment, and this will become increasingly important as the population ages. Thus, it is imperative that new methods be developed for patient stratification based on risk of recurrence to enable appropriate patient management.

BRIEF SUMMARY OF THE INVENTION

The present invention provides for methods for determining the risk of metastasis of cancer in an individual who has or had prostate cancer. In some embodiments, the methods comprise detecting in a tumor sample from the individual the number of copies per cell of genomic DNA at least one genomic location selected from the group consisting of 2qtel, 3q26.2, 3q26.32, 5p15.1, 7p22.3, 7q11.23, 7q11.22, 7q22.1, 7q31.31, 9q34.11, 11p15.5, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14 and 16q23.1, wherein an increase in the number of copies per cell of DNA in genomic locations selected from the group consisting of 2qtel, 3q26.2, 3q26.32, 5p15.1, 7p22.3, 7q11.23, 7q11.22, 7q22.1, 7q31.31, 9q34.11, 11p15.5, 17q21.33, 17q25.3 and 22q13.1 and/or a decrease in the number of copies per cell of DNA in genomic locations selected from the group consisting of 4p13, 5q13.1, 5q14.3, 5q21.1, 5q21.2, 5q21.3, 5q23.1, 6q14.1, 6q21, 8p22, 8p21.2, 8 p12, 10q23.31, 13q14.11, 13q14.13, 13q14.2, 13q14 and 16q23.1, compared to the number of copies per cell in non-cancer cells, indicates an increased risk of metastasis.

In some embodiments, the number of copies per cell of at least one of the above genomic regions and the number of copies per cell of 8p23.2 and/or 11q13.1 are determined.

In some embodiments, the methods comprise detecting the number of copies per cell at least 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 of the genomic locations. In some embodiments, the methods comprise detecting the number of copies per cell at 2qtel, 3q26.2, 3q26.32, 5p15.1, 7p22.3, 7q11.23, 7q11.22, 7q22.1, 7q31.31, 9q34.11, 11p15.5, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14 and 16q23.1. In some embodiments, the methods comprise also detecting the number of copies per cell of MEN1 and/or CSMD1.

In some embodiments, the methods comprise detecting the number of copies of genomic DNA that hybridizes to at least one BAC selected from the group consisting of CTB-172113, RP11-1146E5, RP11-114M1, RP1-97B16, RP11-88L18, RP11-23D23, CTC-329F6, RP1-117G9, RP11-96O16, RP11-213E22, CTD-2041G23, RP11-17O4, RP4-693L23, RP5-1071I14, RP11-46E14, RMC22P003, RP11-25305, RP11-267K19, RP11-135F5, RP11-203J7, RP11-115L24, CTD-2079J2, RP11-73N22, RP11-217L13, RP11-28L24, RP11-47E20, RP11-182G2, RP11-76B12, RP11-232J22, CTD-2015D3, RP11-57I3, RP11-129G17, RP11-14A4, CTD-2202J2, RP11-17I11, RP11-217H23, CTD-2173J2, RP1-269F22, and RP11-12H11.

In some embodiments, the methods comprise detecting the number of copies of genomic DNA in a gene encoding a polypeptide selected from the group consisting of EV11, PIK3CA, EIF3S9, ELN, AUTS2, VGF, Serpine1, PLOD3, AP1S1, CORTBP2, p57 (KIP2), NGFR, CBX4, CBX8, PDGFB, FER, TUBE1, LAMA4, BVES, POPDC3, TUSC3, DOCK5, BNIP3L, ADRA1, NRG1, LHFP, GTF2F2, RB1 and CHC1L.

Alternatively, expression of RNA or protein encoded by the above-described genes is used to determine the risk of metastasis in an individual who has or had prostate cancer.

In some embodiments, at least one of the above-described genes (also listed in Table 2) and the number of copies per cell of MEN1 and/or CSMD1 are determined. In some embodiments, expression of RNA or protein encoded by MEN1 or CSMD1 and expression of RNA or protein encoded by at least one polynucleotide encoding a polypeptide selected from the group consisting of EV11, PIK3CA, EIF3S9, ELN, AUTS2, VGF, Serpine1, PLOD3, AP1S1, CORTBP2, p57 (KIP2), NGFR, CBX4, CBX8, PDGFB, FER, TUBE1, LAMA4, BVES, POPDC3, TUSC3, DOCK5, BNIP3L, ADRA1, NRG1, LHFP, GTF2F2, RB1 and CHC1L are detected.

The present invention also provides methods of determining the stage of a prostate cancer tumor. In some embodiments, the methods comprise detecting in a tumor sample from the individual the quantity of a 8p23.2 polynucleotide, wherein an individual with an advanced stage of prostate cancer has fewer genomic copies of 8p23.2 per cell than a normal individual. In some embodiments, the methods comprise detecting in a tumor sample from the individual the quantity of a CSMD1 polynucleotide or polypeptide, wherein an individual with an advanced stage of prostate cancer has fewer genomic copies of CSMD1 per cell or reduced expression of a CSMD1 mRNA, or reduced expression of a CSDM1 polypeptide than a normal individual.

In some embodiments, the CSMD1 polynucleotide is genomic DNA and a decreased number of copies per cell of the genomic DNA is associated with an advanced stage of prostate cancer. In some embodiments, the CSMD1 polynucleotide is a CSMD1 mRNA or cDNA thereof and decreased expression of the polynucleotide is associated with an advanced stage of prostate cancer.

The present invention also provides methods of assessing the risk of post-prostatectomy reoccurrence of cancer in an individual. In some embodiments, the methods comprise detecting in a tumor sample from the individual the quantity of a 11q13.1 polynucleotide, wherein an individual with a risk of post-prostatectomy reoccurrence of cancer has an increased number of genomic copies of 11q13.1 per cell than a normal individual. In some embodiments, the methods comprise detecting in a tumor sample from the individual the quantity of a MEN1 polynucleotide or MEN1 polypeptide, wherein an individual with a risk of post-prostatectomy reoccurrence of cancer has an increased number of genomic copies of MEN1 per cell, or increased expression of a MEN1 mRNA, or increased expression of a MEN1 polypeptide, than a normal individual. In some embodiments, the methods further comprise detecting a polynucleotide or polypeptide set forth in Table 2.

In some embodiments, the MEN1 polynucleotide is genomic DNA and an increased number of copies per cell of the genomic DNA is associated with a risk of post-prostatectomy reoccurrence of cancer. In some embodiments, the MEN1 polynucleotide is a MEN1 mRNA or cDNA thereof and increased expression of the polynucleotide is associated with a risk of post-prostatectomy reoccurrence of cancer. In some embodiments, the methods further comprise detecting a polynucleotide or polypeptide set forth in Table 2.

The present invention also provides methods of identifying an agent that inhibits prostate cancer proliferation or metastasis. In some embodiments, the methods comprise: contacting a plurality of agents to a cell expressing a polypeptide selected from the group consisting of the gene products listed in Table 2; selecting an agent that modulates expression or activity of the polypeptide (i.e., directly affects polypeptide expression or affects expression indirectly, e.g., by changing transcript accumulation, etc.); and determining whether the selected agent inhibits prostate cancer proliferation or metastasis, thereby identifying an agent that inhibits prostate cancer proliferation or metastasis. The present invention also provides agents selected according to the above method.

The present invention also provides methods of treating prostate cancer or inhibiting metastasis of prostate cancer. In some embodiments, the methods comprise administrating to an individual in need thereof an agent selected according to the above method.

DEFINITIONS

The terms "tumor" or "cancer" in an animal (e.g., a human) refers to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumor, but such cells may also exist in isolation from one another within an animal. "Tumor" includes both benign and malignant neoplasms.

The terms "hybridizing specifically to", "specific hybridization", and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences in a mixed population (e.g., a cell lysate or DNA preparation from a tissue biopy) A "stringent hybridization" and "stringent hybridization wash conditions" in the context of nucleic acid hybridization (e.g., as in array, Southern or nrthern hybridizations) are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, Ch.* 2, "*Overview of principles of hybridization and the strategy of nucleic acid probe assays*," Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell (2001) *Molecular Cloning: A Laboratory Manual* (3rd ed.) Vol. 1-3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

The term "nucleic acid" or "polynucleotide" as used herein refers to a deoxyribonucleotide or ribonucleotide in either single- or double-stranded form. The term encompasses nucleic acids containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189-197. Other synthetic backbones encompassed by the term include methyl-phosphonate linkages or alternating methylphosphonate and phosphodiester linkages (Strauss-Soukup (1997) *Biochemistry* 36: 8692-8698), and benzylphosphonate linkages (Samstag (1996) *Antisense Nucleic Acid Drug Dev* 6: 153-156).

The term "nucleic acid array" as used herein is a plurality of target elements, each target element comprising one or more nucleic acid molecules (probes) immobilized on one or more solid surfaces to which sample nucleic acids can be hybridized. The nucleic acids of a probe can contain sequence(s) from specific genes or clones, e.g. from specific genomic regions described in Table 2 or comprising the 8p23.2 (e.g., CSMD1) or 11q13.1 (e.g., MEN1) locus. Other probes may contain, for instance, reference sequences. The probes of the arrays may be arranged on the solid surface at different densities. The probe densities will depend upon a number of factors, such as the nature of the label, the solid support, and the like. One of skill will recognize that each probe may comprise a mixture of nucleic acids of different lengths and sequences. Thus, for example, a probe may contain more than one copy of a cloned piece of DNA or RNA, and each copy may be broken into fragments of different lengths. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The term "probe" or "nucleic acid probe", as used herein, is defined to be one or more nucleic acid fragments whose specific hybridization to a sample can be detected. The probe may be unlabeled or labeled as described below so that its binding to the target or sample can be detected. The probe is produced from a source of nucleic acids from one or more particular (preselected) portions of a chromosome, e.g., one or more clones, an isolated whole chromosome or chromosome fragment, or a collection of polymerase chain reaction (PCR) amplification products. The probes of the present invention are produced from nucleic acids found in the regions described herein. Often, the probes are centromeric probes, i.e., they hybridize to nucleic acid sequences present in the centromeres of the specific chromosomes, which provide a stronger signal.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) *Science* 767-773; Johnston (1998) *Curr. Biol.* 8: R171-R174; Schummer (1997) *Biotechniques* 23: 1087-1092; Kern (1997) *Biotechniques* 23: 120-124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody or its functional equivalent will be most critical in specificity and affinity of binding. See Paul, *Fundamental Immunology*.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, e.g., pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

DETAILED DESCRIPTION OF THE INVENTION

I. Introduction

Figure 1:
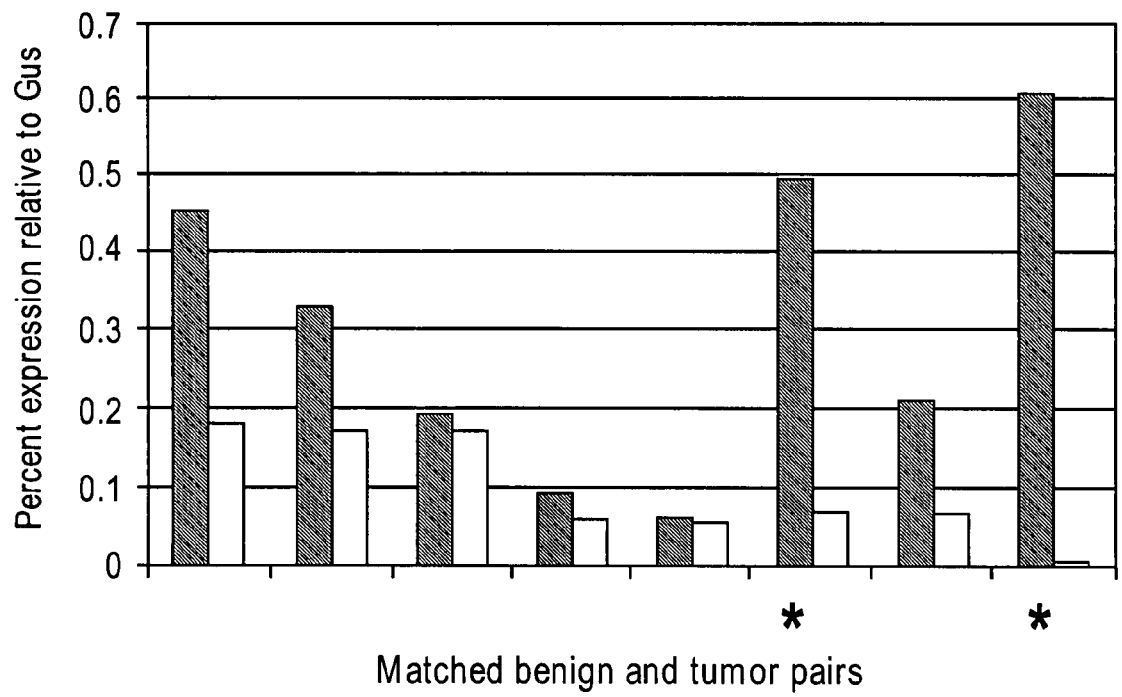
FIG. 1 illustrates real-time RT-PCR expression results for the CSMD1 gene at 8p23. Matched benign and tumor pairs were used in this study and are indicated by black and white bars, respectively. Each tissue sample was run in triplicate. The standard deviation for the cycle threshold values of all three replicates was less than 0.3. Results are displayed relative to a GUS reference gene. An asterisk denotes samples that are stage pT$\geq$3.

The present invention is based in part on the discovery that certain chromosomal copy number aberrations are associated with recurrence and metastasis of prostate cancer. As demonstrated in the examples below, an increase in the number of copies per cell of DNA in genomic locations selected from the group consisting of 2qtel, 3q26.2, 3q26.32, 5p15.1, 7p22.3, 7q11.23, 7q11.22, 7q22.1, 7q31.31, 8p23.2, 9q34.11, 11p15.5, 11q13.1, 17q21.33, 17q25.3 and/or 22q13.1 and/or a decrease in the number of copies per cell of DNA in genomic locations selected from the group consisting of 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14 and/or 16q23.1, compared to the number of copies per cell in non-cancer cells, indicates an increased risk of metastasis of prostate cancer.

Moreover, the inventors have discovered that reduction of expression of CSMD1 or loss of all or part of the CSMD1 gene is associated with an advanced stage of prostate cancer. For example, pathological progressive prostate cancer is associated with the loss of CSMD1. Accordingly, determining the level of expression or the copy number of CSMD1 in a prostate tumor cell is indicative of the stage of cancer.

In addition, the inventors have found that gain of genomic copies of the MEN1 gene or increased MEN1 expression is associated with tumors that reoccurred following prostatectomy. Accordingly, determining the level of expression or the copy number of MEN1 in a prostate tumor cell is useful to predict cancers that are likely to reoccur following prostate surgery.

II. Detecting Chromosomal Region or Parts Thereof.

Genomic instability is a hallmark of solid tumors, and virtually no solid tumor exists that does not show some alterations of the genome. With the vast majority of tumors this instability is expressed at the level of the chromosomal complement, and thus is detectable by cytogenetic approaches (Mitelman, F., *Catalog of Chromosome Aberrations in Cancer*, 5th Edition (New York: Wiley-Liss) (1994)). However, aneuploidy or chromosomal rearrangement per se is not indicative of malignancy and many benign tumors can have an aberrant karyotype (Mitelman, 1994). To efficiently take advantage of chromosomal abnormalities as a marker, it is useful to know characteristic aberrations of the tumors that are to be differentiated.

As discussed in the examples, detection of increases in the number of copies per cell in tumor samples of the following chromosomal locations: 2qtel, 3q26.2, 3q26.32, 5p5.1, 7p22.3, 7q11.23, 7q11.22, 7q22.1, 7q31.31, 9q34.11, 11p15.5, 17q21.33, 17q25.3 and/or 22q13.1, and/or decreases in the number of copies per cell in tumor samples of the following chromosomal locations: 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14 and/or 16q23.1 is indicative of an increased risk of metastasis. These locations may be detected individually, or in combination. Thus, for example, in some embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 of the above-listed chromosomal locations may be detected to predict the risk of metastasis.

A number of the genomic locations of interest in the present invention are bounded by probes as listed below:

| Genomic Location | Boundary BAC clone | Boundary BAC clone |
|---|---|---|
| 2qtel | RP11-118M12 | CTB-228K22 |
| 3q26.2 | RP11-198G24 | RP11-141C22 |
| 3q26.32 | RP11-148D23 | CTB-364E3 |
| 3q26.3 | CTB-364E3 | RP11-118F4 |
| 5p15.1 | RP11-269O14 | RP11-5N11 |
| 7p22.3 | RP1-164D18 | RP11-96L18 |
| 7q11.22 | RP11-170H15 | GS1-35C5 |
| 7q11.23 | CTB-51J22 | RP11-137E8 |
| 7q22.1 | GS1-87A9 | RP4-747G18 |
| 7q31.31 | CTB-185C18 | GS1-74E4 |
| 9q34.1 | RP11-62A6 | CTD-2280C3 |
| 11p15.5 | GS-137C7 | RP11-120E20 |
| 17q21.33 | RP11-110H20 | RP5-32P19 |
| 17q25.3 | RP11-128J1 | CTB-209F23 |
| 22q13.1 | RP11-108C6 | CTD-2194F18 |
| 4p13 | RP11-113F10 | RP11-105F21 |
| 5q13.1 | CTB-134O19 | CTD-2113P14 |
| 5q14.3 | RP11-275E14 | RP11-45O11 |
| 5q21.1-5q21.2 | RP11-204D12 | RP11-277N18 |
| 5q21.3 | RP11-252I13 | RP11-13O21 |
| 5q23.1 | RP11-81C5 | RP11-15P5 |
| 6q14.1 | RP11-28P18 | RP11-32O2 |
| 6q21 | RP11-73D20 | RP11-165E15 |
| 6q21 | RP11-75C8 | RP11-59F18 |
| 8p22 | RP11-236O1 | RP11-274K12 |
| 8p21.2 | RP11-158F9 | RP11-70L1 |
| 8p21.2 | RP11-164H24 | RP11-199N14 |
| 8p21.2 | RP11-199N14 | RP11-138J2 |
| 8p12 | CTD-2020E14 | RP11-122D17 |
| 10q23.31 | CTB-46B12 | RP11-67L13 |
| 13q14.11 | CTD-2037D17 | RP11-53F19 |
| 13q14.11 | RP11-53F19 | RP11-9F13 |
| 13q14.11 | RP11-34K15 | RP11-30N18 |
| 13q14.13 | RP11-30N18 | RP11-52B21 |
| 13q14.2 | RP11-120G8 | RP1-58D13 |
| 13q14.3 | RP1-58D13 | RP11-211J11 |
| 16q23.1 | RP11-217K3 | RP11-284G2 |
| 8p23.1 | CTB-12F4 | RP11-548G17 |
| 11q13.1 | RP11-82K8 | RP11-140K14 |

In addition to the above table, copy number of MEN1 or CSMD1 genes, or genes listed in Table 2 (e.g., coding sequences and/or upstream or downstream elements such as promoters including, but not limited to, nucleotides 5 kb upstream of the initiation of translation or transcription) may also be detected. Coding sequences of MEN1 and CSMD1 are publicly available in Genbank accession numbers U93237 and NM_033225, respectively. Probes for detection of MEN1 and CSMD1 are available commercially from, e.g., Applied Biosystems Inc., Foster City, Calif.).

Single or low-copy number probes that detect DNA within the genomic locations are particularly useful for use in the invention. A list of exemplary BAC clones that may be used to detect or generate probes to detect the various genomic locations is provided in Table 2 in the examples. However, it should be understood that this list is not intended to limit the invention and other probes within the genomic locations can also be used.

Several techniques that permit the study of chromosomal complement are well known in the art. For example, fluorescence in-situ hybridization (FISH) can be used to study copy numbers of individual genetic loci or particular regions on a chromosome (Pinkel et al., *Proc. Natl. Acad. Sci. U.S.A.* 85, 9138-42 (1988)). Comparative genomic hybridization (CGH) (Kallioniemi et al. *Science* 258, 818-21 (1992)) may also be used (Houldsworth et al. *Am J Pathol* 145, 1253-60 (1994)) to probe for copy number changes of chromosomal regions as well as changes in chromosome number.

As appreciated by one of skill in the art, analysis of copy number can be performed using multiple probes to a particular chromosome or can be performed using a single probe, e.g., a centromeric probe, to detect change in copy number. Probes useful in the methods described here are available from a number of sources. For instance, P1 clones are available from the DuPont P1 library (Shepard, et al., *Proc. Natl. Acad. Sci. USA,* 92: 2629 (1994), and available commercially from Genome Systems. Various libraries spanning entire chromosomes are also available commercially (Clonetech, South San Francisco, Calif.), or from the Los Alamos National Laboratory.

In one set of embodiments, the hybridizations are performed on a solid support. For example, probes that selectively hybridize to specific chromosomal regions can be spotted onto a surface. Conveniently, the spots are placed in an ordered pattern, or array, and the placement of the probes on the array is recorded to facilitate later correlation of results. The nucleic acid samples are then hybridized to the array. In one configuration, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606-614; Jackson (1996) *Nature Biotechnology* 14:1685; Chee (1995) *Science* 274: 610; WO 96/17958).

Arrays, particularly nucleic acid arrays can be produced according to a wide variety of methods well known to those of skill in the art (see, e.g., U.S. Pat. No. 6,040,138). For example, in a simple embodiment, "low density" arrays can simply be produced by spotting (e.g. by hand using a pipette) different nucleic acids at different locations on a solid support (e.g. a glass surface, a membrane, etc.).

This simple spotting approach has been automated to produce high density spotted arrays (see, e.g., U.S. Pat. No. 5,807,522). This patent describes the use of an automated systems that taps a microcapillary against a surface to deposit a small volume of a biological sample. The process is repeated to generate high density arrays. Arrays can also be produced using oligonucleotide synthesis technology. Thus, for example, U.S. Pat. No. 5,143,854 and PCT patent publication Nos. WO 90/15070 and 92/10092 teach the use of light-directed combinatorial synthesis of high density oligonucleotide arrays.

In another embodiment the array, particularly a spotted array, can include genomic DNA, e.g. overlapping clones that provide a high resolution scan of the amplicon corresponding to the region of interest. Amplicon nucleic acid can be obtained from, e.g., MACs, YACs, BACs, PACs, P1s, cosmids, plasmids, inter-Alu PCR products of genomic clones, restriction digests of genomic clone, cDNA clones, amplification (e.g., PCR) products, and the like.

In various embodiments, the array nucleic acids are derived from previously mapped libraries of clones spanning or including the target sequences of the invention, as well as clones from other areas of the genome, as described below. The arrays can be hybridized with a single population of sample nucleic acid or can be used with two differentially labeled collections (as with a test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

Target elements of various sizes, ranging from 1 mm diameter down to 1 µm can be used. Smaller target elements containing low amounts of concentrated, fixed probe DNA are used for high complexity comparative hybridizations since the total amount of sample available for binding to each target element will be limited. Thus it is advantageous to have small array target elements that contain a small amount of concentrated probe DNA so that the signal that is obtained is highly localized and bright. Such small array target elements are typically used in arrays with densities greater than $10^4/cm^2$. Relatively simple approaches capable of quantitative fluorescent imaging of 1 $cm^2$ areas have been described that permit acquisition of data from a large number of target elements in a single image (see, e.g., Wittrup, *Cytometry* 16: 206-213, 1994).

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques. Nucleic acids can be conveniently coupled to glass using commercially available reagents. For instance, materials for preparation of silanized glass with a number of functional groups are commercially available or can be prepared using standard techniques (see, e.g., Gait (1984) Oligonucleotide Synthesis: A Practical Approach, IRL Press, Wash., D.C.). Quartz cover slips, which have at least 10-fold lower autofluorescence than glass, can also be silanized.

Alternatively, the samples can be placed in separate wells or chambers and hybridized in their respective well or chambers. The art has developed robotic equipment permitting the automated delivery of reagents to separate reaction chambers, including "chip" and microfluidic techniques, which allow the amount of the reagents used per reaction to be sharply reduced. Chip and microfluidic techniques are taught in, for example, U.S. Pat. No. 5,800,690, Orchid, "Running on Parallel Lines" *New Scientist*, Oct. 25, 1997, McCormick, et al., *Anal. Chem.* 69:2626-30 (1997), and Turgeon, "The Lab of the Future on CD-ROM?" *Medical Laboratory Management Report*. December 1997, p. 1. Automated hybridizations on chips or in a microfluidic environment are contemplated methods of practicing the invention.

Although microfluidic environments are one embodiment of the invention, they are not the only defined spaces suitable for performing hybridizations in a fluid environment. Other such spaces include standard laboratory equipment, such as the wells of microtiter plates, Petri dishes, centrifuge tubes, or the like can be used.

In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. The preferred size range is from about 200 bp to about 1000 bases, more preferably between about 400 to about 800 bp for double stranded, nick translated nucleic acids.

In some applications it is necessary to block the hybridization capacity of repetitive sequences. Thus, in some embodiments, human genomic DNA or Cot-1 DNA is used to block non-specific hybridization.

In Comparative Genomic Hybridization (CGH) methods a first collection of (sample) nucleic acids (e.g. from a possible tumor) is labeled with a first label, while a second collection of (control) nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number.

Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: *In Situ Hybridization Protocols*, Choo, ed., Humana Press, Totowa, N.J. (1994), etc. In some embodiments, the hybridization protocol of Pinkel et al. (1998) *Nature Genetics* 20:207-211 or of Kallioniemi (1992) *Proc. Natl. Acad Sci USA* 89:5321-5325 (1992) is often used.

In general, there is a tradeoff between hybridization specificity (stringency) and signal intensity. Thus, in some embodiments, the wash is performed at the highest stringency that produces consistent results and that provides a signal intensity greater than approximately 10% of the background intensity. Thus, in some embodiments, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In some embodiments, background signal is reduced by the use of a detergent (e.g., C-TAB) or a blocking reagent (e.g., sperm DNA, cot-1 DNA, etc.) during the hybridization to reduce non-specific binding. The hybridization may be performed, for example, in the presence of about 0.1 to about 0.5 mg/ml DNA (e.g., cot-1 DNA). The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology*, Vol. 24: *Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background membranes can be used (see, e.g., Chu (1992) *Electrophoresis* 13:105-114). The sensitivity for detection of spots ("target elements") of various diameters on the candidate membranes can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., membranes, glass, fused silica) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

Other nucleic acid hybridization formats are also known to those skilled in the art. Such formats are described, for example in Sambrook and Russell, supra. These includes analyses such as Southern blotting. The sensitivity of the hybridization assays may also be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Ploidy, i.e., chromosome number, may also be determined using quantitative PCR such as real-time PCR (see, e.g., Suzuki et al., *Cancer Res.* 60:5405-9 (2000)). For example, quantitative microsatellite analysis (QUMA) can be performed for rapid measurement of relative DNA sequence copy number. In QUMA, the copy number of a test locus relative to a pooled reference is assessed using quantitative, real-time PCR amplification of loci carrying simple sequence repeats. Use of simple sequence repeats is advantageous because of the large numbers that are mapped precisely.

Additional protocols for quantitative PCR are provided in Innis et al. (1990) PCR Protocols, A Guide to Methods and Applications, Academic Press, Inc. N.Y.).

Labeling and Detection of Nucleic Acids

The hybridized nucleic acids are typically detected by detecting one or more labels attached to the sample or probe nucleic acids. The labels may be incorporated by any of a number of means well known to those of skill in the art. Means of attaching labels to nucleic acids include, for example nick translation or end-labeling (e.g. with a labeled RNA) by phosphorylating (e.g., with a kinase) of the nucleic acid and subsequent attachment (ligation) of a nucleic acid linker joining the sample nucleic acid to a label (e.g., a fluorophore). A wide variety of linkers for the attachment of labels to nucleic acids are also known. In addition, intercalating dyes and fluorescent nucleotides can also be used.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like, see, e.g., Molecular Probes, Eugene, Oreg., USA), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is useful because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are particularly useful because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence. Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. The nucleic acid probe may also be labeled with digoxigenin and then detected with an antibody that is labeled with a fluorochrom, or an enzyme such as horseradish peroxidase or alkaline phosphatase. For a detailed review of methods of labeling nucleic acids and detecting labeled hybridized nucleic acids see *Laboratory Techniques in Biochemistry and Molecular Biology*, Vol. 24: *Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) *Science*, 281: 2013-2016). Similarly, highly fluorescent quantum dots (zinc sulfide-capped cadmium selenide) have been covalently coupled to biomolecules for use in ultrasensitive biological detection (Warren and Nie (1998) *Science,* 281: 2016-2018).

IV. Detecting Gene Expression

As described above, it has been discovered that increased expression of MEN1 compared to a healthy control indicates a risk of post-prostatectomy re-occurrence of cancer. Moreover, a decrease in CSMD1 expression compared to a healthy control indicates an advanced stage of prostate cancer, i.e., a cancer that is likely an aggressive cancer that will reoccur and/or metastasize. In addition, as displayed in Table 2 in the examples, genomic regions whose increased or decreased copy number are associated with metastasis comprise a number of genes, whose increased or decreased expression, respectively, is associated with metastasis. Accordingly, the present invention provides for methods of detecting expression of MEN1 and/or CSMD1 expression and/or expression of any or all of the genes listed in Table 2, including expression of mRNAs or proteins encoded by the genes.

Typically, the level of a polynucleotide or polypeptide of interest will be detected in a biological sample. A "biological sample" refers to a cell or population of cells or a quantity of tissue or fluid from an animal. Most often, the sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure the cancer-associated polynucleotide or polypeptide levels. Numerous types of biological samples can be used in the present invention, including, but not limited to, a tissue biopsy, a blood sample, a buccal scrape, a saliva sample, or a nipple discharge.

As used herein, a "tissue biopsy" refers to an amount of tissue removed from an animal for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

In one embodiment, the presence of cancer is evaluated by determining the level of expression of mRNA encoding a protein of interest. Methods of evaluating RNA expression of a particular gene are well known to those of skill in the art, and include, inter alia, hybridization and amplification based assays.

Direct Hybridization-Based Assays

Methods of detecting and/or quantifying the level of gene transcripts of interest (mRNA or cDNA made therefrom) using nucleic acid hybridization techniques are known to those of skill in the art. For example, one method for evaluating the presence, absence, or quantity of polynucleotides involves a northern blot. Gene expression levels can also be analyzed by techniques known in the art, e.g., dot blotting, in situ hybridization, RNase protection, probing DNA microchip arrays, and the like.

Amplification-Based Assays

In another embodiment, amplification-based assays are used to measure the expression level of a gene of interest. In such an assay, the nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the level of expression of the gene of interest in the sample. Methods of quantitative amplification are well known to those of skill in the art. Detailed protocols for quantitative PCR are provided, e.g., in Innis et al. (1990) *PCR Protocols, A Guide to Methods and Applications,* Academic Press, Inc. N.Y.). The known nucleic acid sequences for the genes listed herein is sufficient to enable one of skill to routinely select primers to amplify any portion of the gene. Exemplary sequences for the MEN1 and CSMD1 cDNAs can be found in Genbank accession numbers U93236 and NM_033225, respectively. Probes to identify the genomic regions identified in this application include, but are not limited to, the BACs listed in Table 2.

In one embodiment, a TaqMan™ based assay is used to quantify the cancer-associated polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, literature provided by Perkin-Elmer, e.g., www2.perkin-elmer.com).

Other suitable amplification methods include, but are not limited to, ligase chain reaction (LCR) (see, Wu and Wallace (1989) *Genomics* 4: 560, Landegren et al. (1988) *Science* 241: 1077, and Barringer et al. (1990) *Gene* 89: 117), transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

Production of Antibodies and Immunological Detection

Polypeptides encoded by the genes described herein can be detected and/or quantified by any methods known to those of skill in the art. Samples can be from any biological source, including e.g., tissue biopsies, tumors, and bodily fluids such as blood, urine, semen, etc.

In some embodiments, antibodies can also be used to detect polypeptides encoded by the genes described herein. Antibodies to these polypeptides can be produced using well known techniques (see, e.g., Harlow & Lane, *Antibodies: A Laboratory Manual* (1988) and Harlow & Lane, *Using Antibodies* (1999); Coligan, *Current Protocols in Immunology* (1991); Goding, *Monoclonal Antibodies: Principles and Practice* (2d ed. 1986); and Kohler & Milstein, *Nature* 256: 495-497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)). Such antibodies are typically used for diagnostic or prognostic applications, e.g., in the detection of lung or breast cancer.

Polypeptides of the invention or a fragment thereof may be used to produce antibodies specifically reactive with the polypeptide. For example, a recombinant polypeptide or an antigenic fragment thereof, may be isolated. Recombinant protein is a useful immunogen for the production of monoclonal or polyclonal antibodies. Alternatively, a synthetic peptide derived from the sequences disclosed herein and conjugated to a carrier protein can be used as an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Typically, polyclonal antisera with a titer of $10^4$ or greater may be selected and tested for their cross reactivity against proteins other than the polypeptides of interest using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better. For cross-reactivity determination, typically immunoabsorbed antisera may be used in a competitive binding immunoassay to compare a second protein to the polypeptide of interest. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the antigenic protein of interest that is required to inhibit 50% of binding, then the second protein is said to specifically bind to the polyclonal antibodies generated to the SOCS-3 immunogen.

Once specific antibodies are available, binding interactions with the proteins of interest can be detected by a variety of immunoassay methods. For a review of immunological and immuno assay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra).

Immunoassays also often use a labeling agent to specifically bind to and label the complex formed by the antibody and antigen. The labeling agent may itself be one of the moieties comprising the antibody/antigen complex. Thus, the labeling agent may be a labeled polypeptide or a labeled antibody that binds the protein of interest. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Commonly used assays include noncompetitive assays, e.g., sandwich assays, and competitive assays. In competitive assays, the amount of polypeptide present in the sample is measured indirectly by measuring the amount of a known, added (exogenous) polypeptide of interest displaced (competed away) from an antibody that binds by the unknown polypeptide present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41(1986)).

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels, enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize the polypeptide of interest, or secondary antibodies that recognize an antibody that binds the polypeptide.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

V. Identification of Modulators of Genes and Polypeptides of the Invention

Modulators, i.e., inhibitors of those gene products listed as gaining copy number in prostate cancer in Table 2 or MEN1, or activators of those gene products listed as losing copy numbers in prostate cancer in Table 2 or CSMD1, are useful for treating cancer, including prostate cancer. For example, administration of the inhibitors or activators can be used to treat prostate cancer or at least reduce the progression or symptoms of prostate cancer and/or metastasis of the cancer and can be used in combination with prostate surgery or in the absence of surgery.

A. Agents that Modulate Polypeptides Described Herein

The agents tested as modulators of polypeptides of the invention can be any small chemical compound, or a biological entity, such as a protein, sugar, nucleic acid or lipid. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). Modulators also include agents designed to modulate (increase or decrease) the level of mRNA encoding polypeptide (e.g., antisense molecules, ribozymes, DNAzymes, small inhibitory RNAs and the like) or the level of translation from an mRNA (e.g., translation blockers such as an antisense molecules that are complementary to translation start or other sequences on an mRNA molecule). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica-Analytika (Buchs, Switzerland) and the like.

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

B. Methods of Screening for Modulators of the Polypeptides of the Invention

A number of different screening protocols can be utilized to identify agents that modulate the level of expression or activity of a polynucleotide of a polypeptide of the invention in cells, particularly mammalian cells, and especially human cells. In general terms, the screening methods involve screening a plurality of agents to identify an agent that modulates the activity of a polypeptide of the invention by, e.g., binding to the polypeptide, preventing an inhibitor or activator from binding to the polypeptide, increasing association of an inhibitor or activator with the polypeptide, or activating or inhibiting expression of the polypeptide.

Any cell expressing a full-length polypeptide of the invention or a fragment thereof can be used to identify modulators. In some embodiments, the cells are eukaryotic cells lines transformed to express a heterologous polypeptide as listed herein.

1. Polypeptide Binding Assays

Preliminary screens can be conducted by screening for agents capable of binding to polypeptides described herein, as at least some of the agents so identified are likely modulators of a polypeptide of the invention. Binding assays are also useful, e.g., for identifying endogenous proteins that interact with the polypeptides described herein. For example, antibodies or other molecules that bind polypeptides of the invention can be identified in binding assays. Binding assays can involve, but are not limited to, use of isolated polypeptides, crude extracts, or cell-based assays.

Binding assays can involve contacting a polypeptide with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound the polypeptide or displacement of labeled substrates. The polypeptides used in these assays can be naturally expressed, cloned or synthesized.

In addition, mammalian or yeast two-hybrid approaches (see, e.g., Bartel, P. L. et. al. *Methods Enzymol,* 254:241 (1995)) can be used to identify polypeptides or other molecules that interact or bind to the polypeptide when expressed together in a host cell.

2. Polypeptide Activity

Polypeptide activity can be assessed using a variety of in vitro and in vivo assays to determine functional, chemical, and physical effects to identify modulators. T Samples or assays that are treated with a potential inhibitor or activator (e.g., a "test compound") are compared to control samples without the test compound, to examine the extent of modulation. Control samples (untreated with candidate compounds are assigned a relative activity value of 100. Inhibition of the polypeptides of the invention is achieved when the activity value relative to the control is about 90%, optionally 50%, optionally 25-0%. Activation of the polypeptides of the invention is achieved when the activity value relative to the control is at least about 110%, optionally 150%, 500%, or more.

3. Expression Assays

Screening assays for a compound that modulates the expression of polynucleotides and polypeptides described herein are also provided. Screening methods generally involve conducting cell-based assays in which test compounds are contacted with one or more cells expressing one or more polypeptide of the invention, and then detecting an increase or decrease in expression (either transcript or translation product). Assays can be performed with any cells that express a polypeptide.

Expression can be detected in a number of different ways. As described herein, the expression level of a polynucleotide can be determined by probing the mRNA expressed in a cell with a probe that specifically hybridizes with an encoded transcript (or complementary nucleic acid derived therefrom). Alternatively, a polypeptide can be detected using immunological methods, e.g., an assay in which a cell lysate is probed with antibodies that specifically bind to the polypeptide.

Reporter systems can also be used to identify modulators of expression. A variety of different types of cells can be utilized in promoter reporter assays. Cells that do not endogenously express a particular polypeptide of interest can be prokaryotic, but are preferably eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the HEK293, HepG2, COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

4. Validation

Agents that are initially identified by any of the foregoing screening methods can be further tested to validate the activity. Validity of the modulators, for example, can be tested in suitable animal models. The basic format of such methods involves administering a lead compound identified during an initial screen to an animal that serves as a model for human disease (e.g., prostate cancer) and/or determining if expression or activity of a polypeptide or polynucleotide of interest is in fact modulated.

C. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

A molecule of interest (e.g., a polypeptide or polynucleotide, or a modulator thereof) can be bound to the solid-state component, directly or indirectly, via covalent or non-covalent linkage, e.g., via a tag. The tag can be any of a variety of components. In general, a molecule that binds the tag (a tag binder) is fixed to a solid support, and the tagged molecule of interest is attached to the solid support by interaction of the tag and the tag binder.

The invention provides in vitro assays for identifying, in a high throughput format, compounds that can modulate the expression or activity of the genes or polypeptides of the invention. Control reactions that measure polypeptide activity in a cell in a reaction that does not include a potential modulator are optional, as the assays are highly uniform. Such optional control reactions are appropriate and increase the reliability of the assay. Accordingly, in some embodiments, the methods of the invention include such a control reaction. For each of the assay formats described, "no modulator" control reactions that do not include a modulator provide a background level of binding activity.

VI. Pharmaceutical Formulation and Administration

The compositions of the invention can be administered directly to a mammalian subject (e.g., a human) using any route known in the art, including e.g., by injection (e.g., intravenous, intraperitoneal, subcutaneous, intramuscular, or intrademal), inhalation, transdermal application, rectal administration, or oral administration.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part a of prepared food or drug.

Formulations suitable for oral administration can comprise: (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The dose administered to a patient, in the context of the present invention should be sufficient to effect a beneficial response in the subject over time, e.g., at least a reduction of prostate cancer cell growth, proliferation or metastasis. The optimal dose level for any patient will depend on a variety of factors including the efficacy of the specific modulator employed, the age, body weight, physical activity, and diet of the patient, on a possible combination with other drugs, and on the cancer. The size of the dose also will be determined by the existence, nature, and extent of any adverse side-effects that accompany the administration of a particular compound or vector in a particular subject.

VII. Kits

For use in diagnostic, and research applications described above, kits are also provided by the invention. The kits of the invention may comprise any or all of the reagents to perform the methods described herein. In the diagnostic and research applications such kits may include any or all of the following: assay reagents, buffers, nucleic acids that bind to at least one of the genomic regions or genes described herein, hybridization probes and/or primers, antibodies or other moieties that specifically bind to at least one of the polypeptides encoded by the genes described herein, etc.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Example 1

Prostate cancer is the most commonly diagnosed non-cutaneous neoplasm among American males and is the second leading cause of cancer-related death. Prostate specific antigen (PSA) screening has resulted in earlier disease detection yet roughly 30% of men will die of metastatic disease. Slow disease progression, an aging population, and associated morbidity and mortality underscore the need for improved disease classification and therapies. To address these issues, we analyzed a cohort of patients using array comparative genomic hybridization (aCGH). The cohort is comprised of 64 patients half of whom recurred postoperatively. Analysis of the aCGH profiles revealed numerous recurrent genomic copy number aberrations. Specific loss at 8p23.2 was associated with advanced stage disease and gain at 11q13.1 was found to be predictive of postoperative recurrence independent of stage and grade. Moreover, comparison with an independent set of metastases revealed ~40 candidate markers associated with metastatic potential. Copy number aberrations at these loci define metastatic genotypes.

The development of array comparative genomic hybridization (aCGH) has important implications for analysis of tumor genomes as well as for development of predictive biomarkers and identification of genes involved in tumor progression. aCGH allows very high resolution quantitative detection of copy number aberrations in tumor genomes (Bruder, C. E., Hirvela, C., Tapia-Paez, I., Fransson, I., Segraves, R., Hamilton, G., Zhang, X. X., Evans, D. G., Wallace, A. J., Baser, M. E. et al. (2001) High resolution deletion analysis of constitutional DNA from neurofibromatosis type 2 (NF2) patients using microarray-CGH. *Hum. Mol. Genet.*, 10:271-282; Hui, A. B., Lo, K. W., Teo, P. M., To, K. F. and Huang, D. P. (2002) Genome wide detection of oncogene amplifications in nasopharyngeal carcinoma by array based comparative genomic hybridization. *Int. J. Oncol.*, 20:467-473; Hui, A. B., Lo, K. W., Yin, X. L., Poon, W. S. and Ng, H. K. (2001) Detection of multiple gene amplifications in glioblastoma multiforme using array-based comparative genomic hybridization. *Lab. Invest.*, 81:717-723; Pinkel, D., Segraves, R., Sudar, D., Clark, S., Poole, I., Kowbel, D., Collins, C., Kuo, W. L., Chen, C., Zhai, Y. et al. (1998) High resolution analysis of DNA copy number variation using comparative genomic hybridization to microarrays. *Nat. Genet.*, 20:207-211; Veltman, J. A., Fridlyand, J., Pejavar, S., Olshen, A. B., Korkola, J. E., DeVries, S., Carroll, P., Kuo, W. L., Pinkel, D., Albertson, D. et al. (2003) Array-based comparative genomic hybridization for genome-wide screening of DNA copy number in bladder tumors. *Cancer Res.*, 63:2872-2880; Snijders, A. M., Nowee, M. E., Fridlyand, J., Piek, J. M., Dorsman, J. C., Jain, A. N., Pinkel, D., van Diest, P. J., Verheijen, R. H. and Albertson, D. G. (2003) Genome-wide-array-based comparative genomic hybridization reveals genetic homogeneity and frequent copy number increases encompassing CCNE1 in fallopian tube carcinoma. *Oncogene*, 22:4281-4286); moreover, associations with clinical outcome can be made (Wilhelm, M., Veltman, J. A., Olshen, A. B., Jain, A. N., Moore, D. H., Presti, J. C., Jr., Kovacs, G. and Waldman, F. M. (2002) Array-based comparative genomic hybridization for the differential diagnosis of renal cell cancer. *Cancer Res.*, 62:957-960). Recurrent copy number changes reveal loci encoding tumor suppressors and oncogenes, the identification of which is now facilitated by completion of the human genome sequence and an impressive repertoire of genome annotation tools (Volik, S., Zhao, S., Chin, K., Brebner, J. H., Herndon, D. R., Tao, Q., Kowbel, D., Huang, G., Lapuk, A., Kuo, W. L. et al. (2003) End-sequence profiling: sequence-based analysis of aberrant genomes. *Proc. Natl. Acad. Sci. U.S.A.,* 100: 7696-7701; Kent, W. J., Sugnet, C. W., Furey, T. S., Roskin, K. M., Pringle, T. H., Zahler, A. M. and Haussler, D. (2002) The human genome browser at UCSC. *Genome Res.,* 12:996-1006).

The arrays used in this study contain ~2400 BAC clones and have an average genome-wide resolution of 1.4 Mb (Snijders, A. M., Nowak, N., Segraves, R., Blackwood, S., Brown, N., Conroy, J., Hamilton, G., Hindle, A. K., Huey, B., Kimura, K. et al. (2001) Assembly of microarrays for genome-wide measurement of DNA copy number. *Nat. Genet.,* 29:263-264; Pinkel, D., Segraves, R., Sudar, D., Clark, S., Poole, I., Kowbel, D., Collins, C., Kuo, W. L., Chen, C., Zhai, Y. et al. (1998) High resolution analysis of DNA copy number variation using comparative genomic hybridization to microarrays. *Nat. Genet.,* 20:207-211). To maximize the clinical utility of data collected from aCGH experiments, clinical specimens are obtained from patients with substantial follow-up. Thus, we developed a methodology for performing aCGH with DNA extracted from archived prostate tumors that were formalin-fixed and paraffin-embedded (Paris, P. L., Albertson, D. G., Alers, J. C., Andaya, A., Carroll, P., Fridlyand, J., Jain, A. N., Kamkar, S., Kowbel, D., Krijtenburg, P. J. et al. (2003) High-resolution analysis of paraffin-embedded and formalin-fixed prostate tumors using comparative genomic hybridization to genomic microarrays. *Am J Pathol,* 162:763-770). To limit the impact of tumor heterogeneity on the sensitivity of aberration detection, we used a novel tumor microdissection method (Paris, P. L., Albertson, D. G., Alers, J. C., Andaya, A., Carroll, P., Fridlyand, J., Jain, A. N., Kamkar, S., Kowbel, D., Krijtenburg, P. J. et al. (2003) High-resolution analysis of paraffin-embedded and formalin-fixed prostate tumors using comparative genomic hybridization to genomic microarrays. *Am J Pathol,* 162:763-770) and tumor specific signal thresholding (see Materials and Methods).

In the current study, aCGH was used to analyze 64 tumors from men at intermediate to high risk of recurrence following radical prostatectomy. This cohort is comprised of 32 patients who biochemically progressed following prostatectomy and 32 who did not. Rising PSA following prostatectomy was used as a biochemical marker of disease recurrence. This unique cohort has a median clinical follow-up of 11 years for non-progressors (ranging from 8 to 15 years), which is longer than the time to recurrence for all progressors (ranging from <1 to 8 years), thereby increasing our confidence in outcome classification.

Our previous work demonstrated that analysis of archived prostate tissue by aCGH is capable of detecting single copy changes (Paris, P. L., Albertson, D. G., Alers, J. C., Andaya, A., Carroll, P., Fridlyand, J., Jain, A. N., Kamkar, S., Kowbel, D., Krijtenburg, P. J. et al. (2003) High-resolution analysis of paraffin-embedded and formalin-fixed prostate tumors using comparative genomic hybridization to genomic microarrays. *Am J Pathol,* 162:763-770). In the present study, aCGH was performed to identify genomic profiles capable of distinguishing indolent from aggressive tumors and loci linked to tumor progression. Because aCGH is performed on arrayed BAC clones with known genome "addresses", it is theoretically possible to identify multiple BAC-based markers of disease progression (Wilhelm, M., Veltman, J. A., Olshen, A. B., Jain, A. N., Moore, D. H., Presti, J. C., Jr., Kovacs, G. and Waldman, F. M. (2002) Array-based comparative genomic hybridization for the differential diagnosis of renal cell cancer. *Cancer Res.,* 62:957-960; O'Hagan, R. C., Brennan, C. W., Strahs, A., Zhang, X., Kannan, K., Donovan, M., Cauwels, C., Sharpless, N. E., Wong, W. H. and Chin, L. (2003) Array Comparative Genome Hybridization for Tumor Classification and Gene Discovery in Mouse Models of Malignant Melanoma. *Cancer Res.,* 63:5352-5356; Albertson, D. G. and Pinkel, D. (2003) Genomic microarrays in human genetic disease and cancer. *Hum. Mol. Genet.,* 12 Suppl 2:R145-152; Massion, P. P., Kuo, W. L., Stokoe, D., Olshen, A. B., Treseler, P. A., Chin, K., Chen, C., Polikoff, D., Jain, A. N., Pinkel, D. et al. (2002) Genomic copy number analysis of non-small cell lung cancer using array comparative genomic hybridization: implications of the phosphatidylinositol 3-kinase pathway. *Cancer Res.,* 62:3636-3640; Omtoft, T. F., Thykjaer, T., Waldman, F. M., Wolf, H. and Celis, J. E. (2002) Genome-wide study of gene copy numbers, transcripts, and protein levels in pairs of non-invasive and invasive human transitional cell carcinomas. *Mol. Cell Proteomics,* 1:37-45).

To extend this study, we included an independent set of metastases in an exploratory exercise to determine whether markers present in primary tumors might be predictive of occult metastasis or proclivity for metastasis. In addition, their inclusion allows identification of known cancer related genes and/or novel genes that may play a direct role in metastasis, and may aid in defining new therapeutic approaches. Finally, an ability to compare patterns of recurrent copy number changes in nonrecurring primary tumors, primary tumors that metastasize, and metastatic tumors may provide important insights into the evolution of prostate cancer.

Results:

Recurrent Copy Number Aberrations

Tumor based thresholds were calculated for all samples. Theoretically a $\log_2$ratio of 0.5 represents a single copy gain and a $\log_2$ratio of −1 corresponds to loss of one copy. However, a number of factors impact on this theoretical value that include the amount of contaminating normal tissue and stroma. The $\log_2$ratio thresholds ranged from an absolute value cut-off of 0.19 to 0.52, with an average of 0.34. A subset of 10 samples was also analyzed with CGH to metaphase chromosomes, and the two techniques were concordant.

The overall frequency of copy number changes in the cohort of 64 primary tumors was determined. The most frequent gains (>40%) in both groups include 11p15.4 (66%), 2p25.1 (60%), 13q34 (60%), 11q13.1 (52%), and 2p22.1 (45%). Frequently (>40%) lost loci were 8p21.2 (46%) and 8p23.2 (45%). Based on the July 2003 freeze of the UCSC human genome browser (http://genome.ucsc.edu/cgi-bin/hg-Gateway), the genomic position of these copy number aberrations correspond to: 2p22 (37891432-39128299), 2p25 (9619095-11073793), 11p15 (9238525-11610583), 11q13 (63810754-66394362), 13q34 (109071421-111904343), 8p21.219764266-25211627), 8p23 (2080710-4357590).

As expected, tumors that progressed had significantly more aberrations (Wilcoxon rank sum p-value p=0.006) than those that did not. The median value for the aberrations for the non-progressors was 10.5 (range 1-56) and 20.5 for progressors (range 1-90). BAC clones that differed by ≧10% in their frequency of copy number gain or loss between the progressors and non-progressors were identified.

Deletion of 8p23 is Associated with Advanced Stage

Deletion of 8p23 was more common in progressors than in non-progressors (50% versus 31%). An association was found between pathological advanced stage disease (pT>3) and loss of 8p (p=0.0015). A possible homozygous loss was seen for BAC RP11-112F7 on 8p23.2 (UCSC July 2003 freeze: 3284324-3324954). The deletion with the greatest magnitude corresponded to a log2ratio of −0.670. The minimal region of loss is ~1 Mb and overlaps exons 3 through 11 of the CUB and Sushi multiple domains 1 (CSMD1) gene. A TaqMan primer-probe set was designed for CSMD1. On a panel of 8 RNAs (6 pT2, 2 pT3) from a separate cohort of prostatectomy patients, CSMD1 showed a marked decrease in expression for the patients of higher stage (pT>3) disease. See FIG. 1.

Gain at 11q13.1 Predicts Recurrence Independent of Stage and Grade

Figure 2:
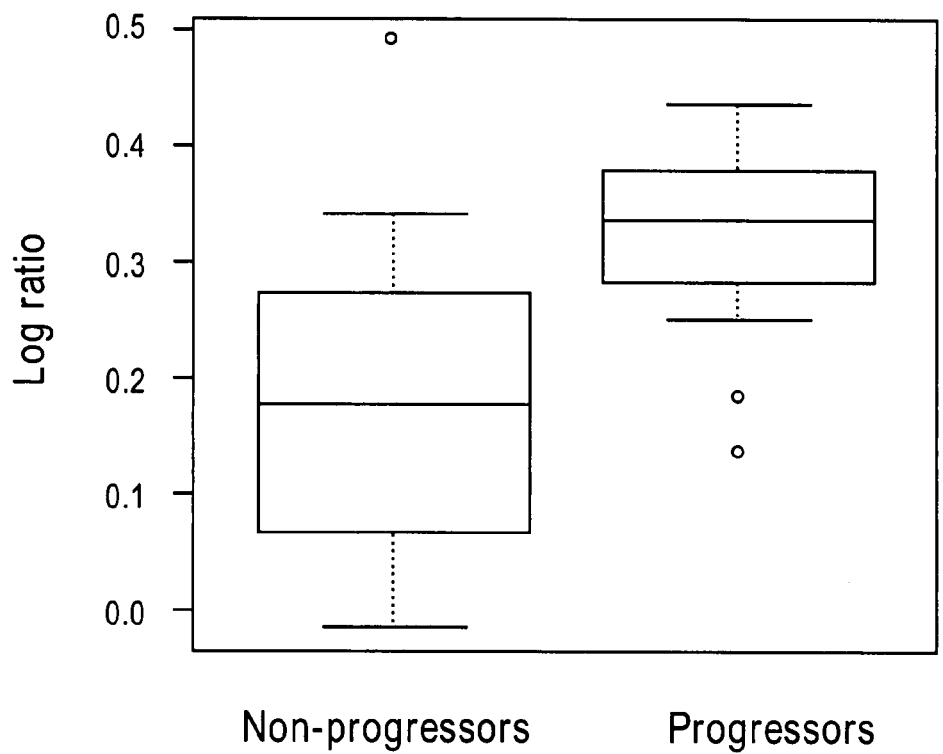
FIG. 2 illustrates a box plot for BAC CTD-2220I9 in negative margin cases. The boxplot compares the distribution of the log$_2$ratios of CTD-2220I9 between progressors and non-progressors for those with negative surgical margins. The solid horizontal lines are $1^{st}$, $2^{nd}$ (median) and $3^{rd}$ quartiles, respectively. The whiskers extend to 1.5 SD away from the median where SD is a distribution of the value in a subgroup for this clone. The outlying points indicate outliers (further than 1.5 SD away from the median).

Univariate analysis indicated a statistically significant association with BAC CTD-222019 on 11q13.1 (UCSC July 2003 freeze: 64313688-64470546) and biochemical failure status, p<0.002. This association was even stronger in the subgroup of 39 samples with negative surgical resection margins. Importantly, the 11q13.1 biomarker retained its significance when adjusted for the clinical parameters (grade, stage, age at operation, margin and preoperative PSA). Distribution of the $\log_2$ratios for that clone in the negative margin cases is shown for progressors and non-progressors in FIG. 2.

Figure 3:
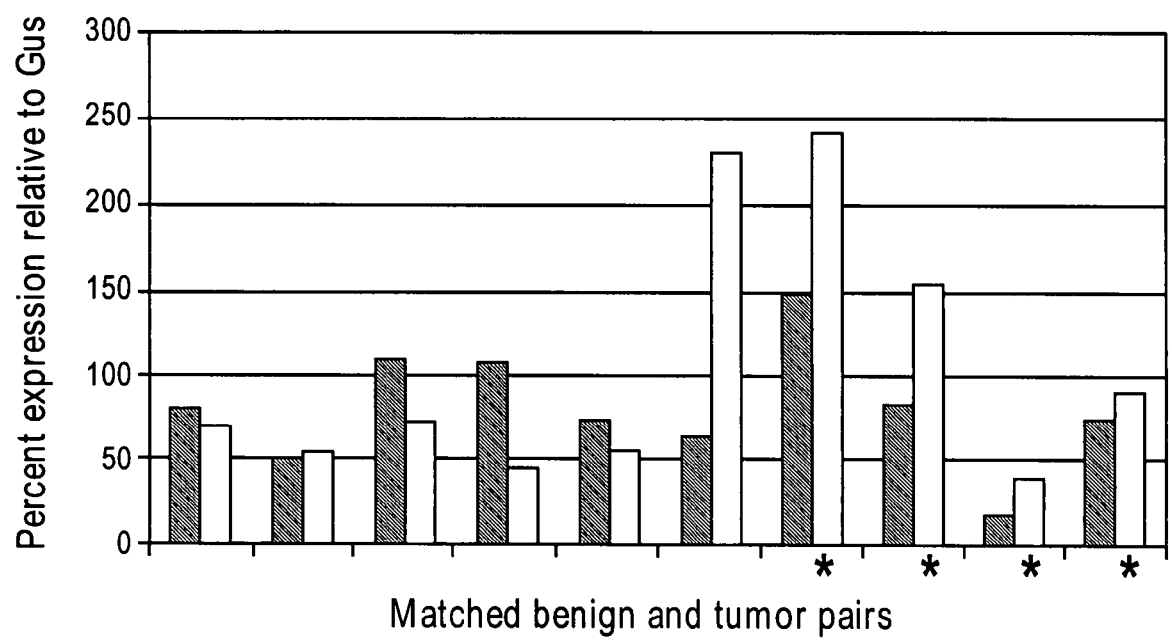
FIG. 3 illustrates real-time RT-PCR expression results for the MEN1 gene at 11q13. Matched benign and tumor pairs were used in this study and are indicated by black and white bars, respectively. Each tissue sample was run in triplicate. The standard deviation for the cycle threshold values of all three replicates was less than 0.3. Results are displayed relative to a GUS reference gene. An asterisk denotes samples that showed genomic gain at 11q13 by aCGH.

The minimal region of the 11q13 amplicon is ~600 kb. This region of the genome is gene rich (17 genes and 4790 ESTs represented in 53 Unigene clusters). The candidate genes that overlap with BAC CTD-222019 are MAP4K2 (mitogen-activated protein kinase kinase kinase kinase 2), MEN1 (multiple endocrine neoplasia I), SF1 (splicing factor 1), PPP2R5B (protein phosphatase 2, regulatory subunit B (B56), beta isoform), NAALADASEL (N-acetylated alpha-linked acidic dipeptidase-like) and EHD1 (EH-domain containing 1). The newly available Oncomine cancer expression database was queried for each of these 6 genes to prioritize candidate genes (Rhodes, D. R., Yu, J., Shanker, K., Deshpande, N., Varambally, R., Ghosh, D., Barrette, T., Pandey, A. and Chinnaiyan, A. M. ONCOMINE: A Cancer Microarray Database and Data-Mining Platform. Neoplasia, in press). There was no difference in SF1 and EHD1 expression levels for radical prostatectomy patients based on PSA recurrence (Singh, D., Febbo, P. G., Ross, K., Jackson, D. G., Manola, J., Ladd, C., Tamayo, P., Renshaw, A. A., D'Amico, A. V., Richie, J. P. et al. (2002) Gene expression correlates of clinical prostate cancer behavior. Cancer Cell, 1:203-209). In primary and metastatic tumors, there was no difference in expression for NAALADASEL and a decrease in PPP2R5B expression for metastatic tumors was observed (Ramaswamy, S., Tamayo, P., Rifkin, R., Mukherjee, S., Yeang, C. H., Angelo, M., Ladd, C., Reich, M., Latulippe, E., Mesirov, J. P. et al. (2001) Multiclass cancer diagnosis using tumor gene expression signatures. Proc. Natl. Acad. Sci. U.S.A., 98:15149-15154; LaTulippe, E., Satagopan, J., Smith, A., Scher, H., Scardino, P., Reuter, V. and Gerald, W. L. (2002) Comprehensive gene expression analysis of prostate cancer reveals distinct transcriptional programs associated with metastatic disease. Cancer Res., 62:4499-4506). Only MEN1 and MAP4K2 showed a trend towards an increase in expression for progressors versus non-progressors (Dhanasekaran), S. M., Barrette, T. R., Ghosh, D., Shah, R., Varambally, S., Kurachi, K., Pienta, K. J., Rubin, M. A. and Chinnaiyan, A. M. (2001) Delineation of prognostic biomarkers in prostate cancer. Nature, 412:822-826). Real-time expression analysis was performed for both MEN1 and MAP4K2. On a panel of 10 RNAs from a separate set of radical prostatectomy patients, only MEN1 showed increased expression (FIG. 3).

Four of the five cases where MEN1 was upregulated also showed an increase in copy number at 11q13 by aCGH. In one tumor MEN1 was overexpressed despite normal copy number.

Identification of Candidate Markers of Metastasis

Figure 4:
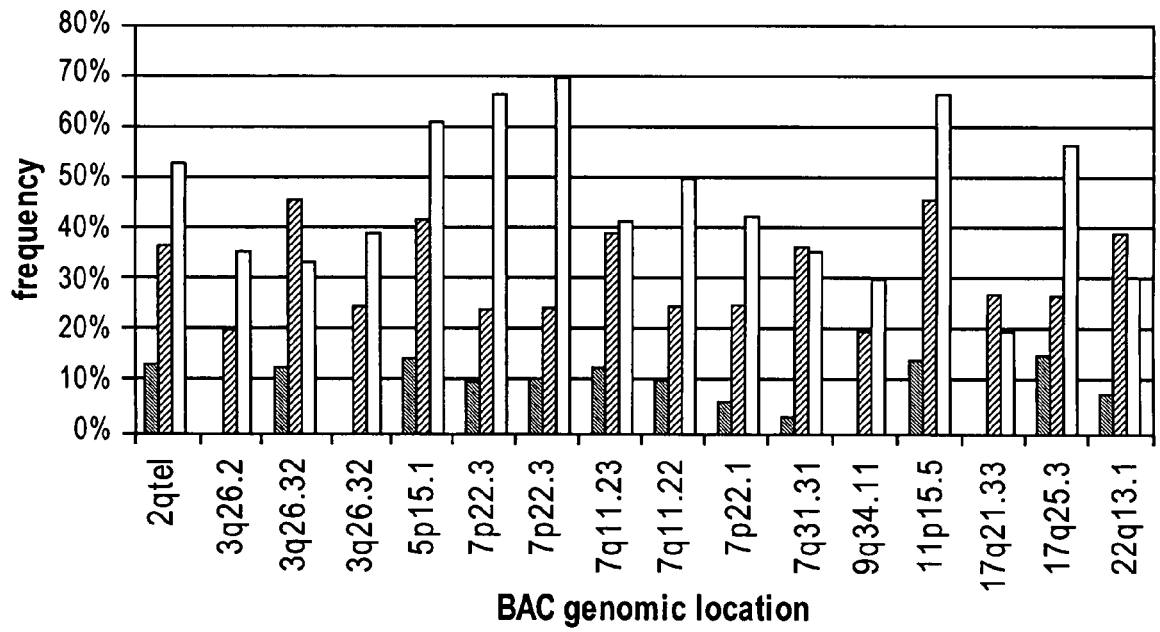
FIG. 4 illustrates a set of 39 candidate BAC biomarkers associated with metastasis. Black bars represent tumors from patients ($N_{max}=32$) who did not progress. Gray bars correspond to primary tumors from patients ($N_{max}=12$) who progressed to metastasis. Tumors represented by the black and gray bars are from a single cohort, whereas white bars represent an independent cohort of metastatic tumors ($N_{max}=15$). Copy number changes are reported only if they occur in each metastatic cohort at a frequency of $\geq 20\%$ and in the non-progressor cohort<20% and were statistically significant ($p \leq 0.05$). 1=EVI1 locus, 2=LIMK1 locus, 3=PDGFB locus, 4=PTEN locus, 5=RB locus.
Figure 4:
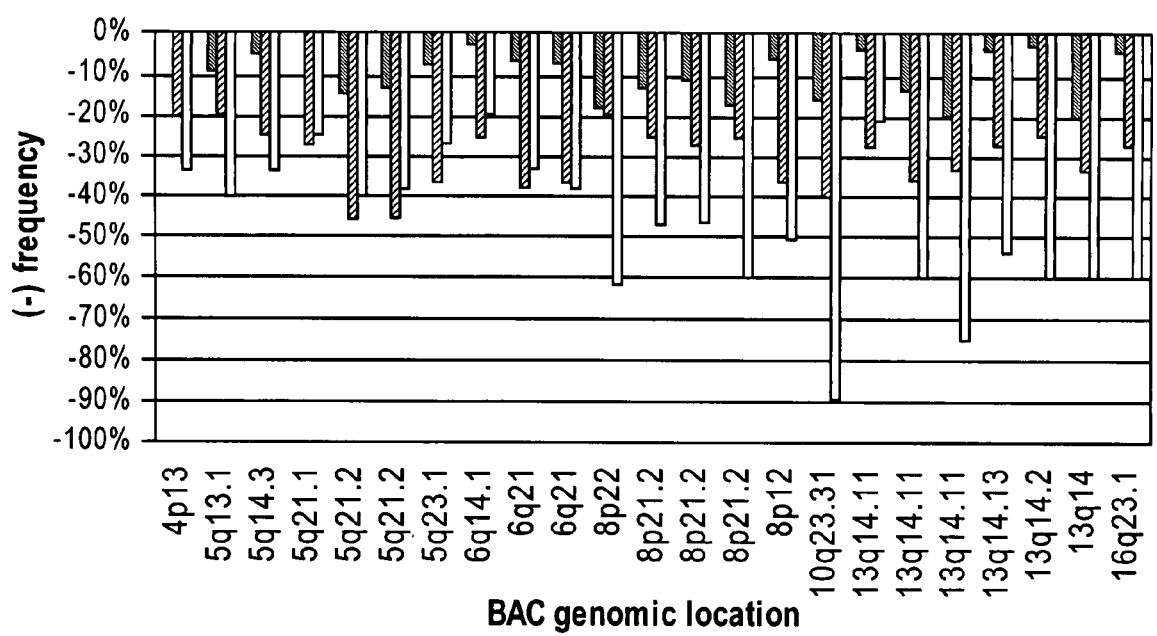

The clinical information for the progressors consisted of recurrence type, which led us to look for BAC-based predictors of distant metastases. A set of organ metastases was used to identify copy number changes that confer a more aggressive phenotype on primary tumors. FIG. 4 shows the result of the analysis of copy number changes in primary tumors that ultimately metastasized and organ metastases versus non-progressors. Only those BAC clones with a p-value of 0.05 or less between primary tumors that metastasized, organ metastases, and non-progressing primary tumors are shown. Approximately forty loci were identified that were infrequently (0%-20%) altered in primary tumors that did not progress. In contrast, aberrations at these loci were frequent in primary tumors that metastasized (20%-45%) and organ metastases (20%-90%). It is noteworthy that six BAC clones were never aberrant in the non-progressor cohort ($N_{max}$=32) but were (20-30%) in both metastatic cohorts.

Discussion:

To maximize both biological information and clinical correlates, tumor based thresholds were used for the determination of aCGH gains and losses. Using spot checks, we confirmed that samples with the smallest threshold corresponded to aCGH data with extremely good signal to noise and vice versa for the sample with the largest threshold value. The tumor based threshold method allowed data with varying signal to noise ratios to be compared to one another. It should be noted that when a BAC was gained in one cohort it was rarely seen to also be deleted in the same cohort. This demonstrates the good signal to noise obtained with our whole genome aCGH technique.

Previously reported and frequently changed loci in prostate cancer +2p22.1 (Cher, M. L., Bova, G. S., Moore, D. H., Small, E. J., Carroll, P. R., Pin, S. S., Epstein, J. I., Isaacs, W. B. and Jensen, R. H. (1996) Genetic alterations in untreated metastases and androgen-independent prostate cancer detected by comparative genomic hybridization and allelotyping. Cancer Res., 56:3091-3102), +11q13.1 (El Gedaily, A., Bubendorf, L., Willi, N., Fu, W., Richter, J., Moch, H., Mihatsch, M. J., Sauter, G. and Gasser, T. C. (2001) Discovery of new DNA amplification loci in prostate cancer by comparative genomic hybridization. Prostate, 46:184-190), − 8p21.2 (Swalwell, J. I., Vocke, C. D., Yang, Y., Walker, J. R., Grouse, L., Myers, S. H., Gillespie, J. W., Bostwick, D. G., Duray, P. H., Linehan, W. M. et al. (2002) Determination of a minimal deletion interval on chromosome band 8p21 in sporadic prostate cancer. Genes Chromosomes Cancer, 33:201-205), −8p21.3 (Oba, K., Matsuyama, H., Yoshihiro, S., Kishi, F., Takahashi, M., Tsukamoto, M., Kinjo, M., Sagiyama, K. and Naito, K. (2001) Two putative tumor suppressor genes on chromosome arm 8p may play different roles in prostate cancer. Cancer Genet. Cytogenet., 124:20-26) and −8p23.2 (Washburn, J. G., Wojno, K. J., Dey, J., Powell, I. J. and Macoska, J. A. (2000) 8pter-p23 deletion is associated with racial differences in prostate cancer outcome. Clin. Cancer Res., 6, 4647-4652) were also identified in this study, and often at higher resolution. Generally, the progressors exhibited a higher frequency of change for these loci. Newly defined amplicons in prostate tumors include 2p25.1, 11p15.4 and 13q34. We observed the expected wide range of inter-tumor heterogeneity in copy number aberration size at these loci. This phenomenon is well known and may reflect utilization of different fragile sites, independent mechanisms of aberration formation, and/or biological selection. In this study BAC clones at the 8p23 deletion and 11q13 gain were identified computationally as having associations with the clinical phenotypes of tumor stage and recurrence, respectively. Individual chromosome specific profiles were then used to define minimum recurrent aberrations identifying MEN1 and CSMD1.

Deletions along 8p are common in prostate cancer (Swalwell, J. I., Vocke, C. D., Yang, Y., Walker, J. R., Grouse, L., Myers, S. H., Gillespie, J. W., Bostwick, D. G., Duray, P. H., Linehan, W. M. et al. (2002) Determination of a minimal deletion interval on chromosome band 8p21 in sporadic prostate cancer. *Genes Chromosomes Cancer,* 33:201-205; Oba, K., Matsuyama, H., Yoshihiro, S., Kishi, F., Takahashi, M., Tsukamoto, M., Kinjo, M., Sagiyama, K. and Naito, K. (2001) Two putative tumor suppressor genes on chromosome arm 8p may play different roles in prostate cancer. *Cancer Genet. Cytogenet.,* 124:20-26; Washburn, J. G., Wojno, K. J., Dey, J., Powell, I. J. and Macoska, J. A. (2000) 8pter-p23 deletion is associated with racial differences in prostate cancer outcome. *Clin. Cancer Res.,* 6, 4647-4652). Whole arm deletion of 8p strongly associated with higher pathologic stage disease in our study. In a recent prostate study, 8p was found to be the most valuable predictor of stage (Chu, L. W., Troncoso, P., Johnston, D. A. and Liang, J. C. (2003) Genetic markers useful for distinguishing between organ-confined and locally advanced prostate cancer. *Genes Chromosomes Cancer,* 36:303-312). Our findings confirm and extend these previous studies.

The identified 8p biomarkers will aid in therapy determination at the time of a biopsy. The deleted 8p23 BAC clones on the genomic array overlap with a single gene called CSMD1 (Sun, P. C., Uppaluri, R., Schmidt, A. P., Pashia, M. E., Quant, E. C., Sunwoo, J. B., Gollin, S. M. and Scholnick, S. B. (2001) Transcript map of the 8p23 putative tumor suppressor region. *Genomics,* 75:17-25; Toomes, C., Jackson, A., Maguire, K., Wood, J., Gollin, S., Ishwad, C., Paterson, I., Prime, S., Parkinson, K., Bell, S. et al. (2003) The presence of multiple regions of homozygous deletion at the CSMD1 locus in oral squamous cell carcinoma question the role of CSMD1 in head and neck carcinogenesis. *Genes Chromosomes Cancer,* 37:132-140). This is the first report of CSMD1 undergoing deletion in prostate cancer. This finding is supported by prostate cancer expression microarray experiments that found CSMD1 decreased expression to be associated with relapse and survival (Henshall, S. M., Afar, D. E., Hiller, J., Horvath, L. G., Quinn, D. I., Rasiah, K. K., Gish, K., Willhite, D., Kench, J. G., Gardiner-Garden, M. et al. (2003) Survival analysis of genome-wide gene expression profiles of prostate cancers identifies new prognostic targets of disease relapse. *Cancer Res.,* 63:4196-4203). Sushi domains exist in adhesion proteins, and therefore make CSMD1 a likely target for deletion by an aggressive tumor. In a recent aCGH study of 14 fallopian tumors, 12 tumors showed deletion involving the CSMD1 region (Snijders, A. M., Nowee, M. E., Fridlyand, J., Piek, J. M., Dorsman, J. C., Jain, A. N., Pinkel, D., van Diest, P. J., Verheijen, R. H. and Albertson, D. G. (2003) Genome-wide-array-based comparative genomic hybridization reveals genetic homogeneity and frequent copy number increases encompassing CCNE1 in fallopian tube carcinoma. *Oncogene,* 22:4281-4286). The minimal region of recurrent loss in their study directly overlapped ours (RP11-82K8 to RP11-140K14). TaqMan results, in a separate cohort of patients, provided further evidence for a decrease in CSMD1 expression in higher stage (pT$\geq$3) prostate tumors. In addition to being a marker of advanced stage disease, deletion of 8p23.2 may be a marker of disease recurrence and therefore warrants future studies. There is considerable evidence implicating the NKX3.1 gene at 8p21 as a tumor suppressor gene in prostate cancer (Xu, L. L., Srikantan, V., Sesterhenn, I. A., Augustus, M., Dean, R., Moul, J. W., Carter, K. C. and Srivastava, S. (2000) Expression profile of an androgen regulated prostate specific homeobox gene NKX3.1 in primary prostate cancer. *J. Urol.,* 163:972-979; Bhatia-Gaur, R., Donjacour, A. A., Sciavolino, P. J., Kim, M., Desai, N., Young, P., Norton, C. R., Gridley, T., Cardiff, R. D., Cunha, G. R. et al. (1999) Roles for Nkx3.1 in prostate development and cancer. *Genes Dev.,* 13:966-977; He, W. W., Sciavolino, P. J., Wing, J., Augustus, M., Hudson, P., Meissner, P. S., Curtis, R. T., Shell, B. K., Bostwick, D. G., Tindall, D. J. et al. (1997) A novel human prostate-specific, androgen-regulated homeobox gene (NKX3.1) that maps to 8p21, a region frequently deleted in prostate cancer. *Genomics,* 43:69-77). CSMD1 and NKX3.1 map ~18 Mb apart in noncontiguous deletions, and thus represent independent tumor suppressor genes.

Previous studies have identified loci that associate with aggressive behavior for prostate cancer (Neville, P. J., Conti, D. V., Krumroy, L. M., Catalona, W. J., Suarez, B. K., Witte, J. S. and Casey, G. (2003) Prostate cancer aggressiveness locus on chromosome segment 19q12-q13.1 identified by linkage and allelic imbalance studies. *Genes Chromosomes Cancer,* 36:332-339; Neville, P. J., Conti, D. V., Paris, P. L., Levin, H., Catalona, W. J., Suarez, B. K., Witte, J. S. and Casey, G. (2002) Prostate cancer aggressiveness locus on chromosome 7q32-q33 identified by linkage and allelic imbalance studies. *Neoplasia,* 4:424-431; Witte, J. S., Goddard, K. A., Conti, D. V., Elston, R. C., Lin, J., Suarez, B. K., Broman, K. W., Burmester, J. K., Weber, J. L. and Catalona, W. J. (2000) Genomewide scan for prostate cancer-aggressiveness loci. *Am. J. Hum. Genet.,* 67:92-99; Takahashi, S., Shan, A. L., Ritland, S. R., Delacey, K. A., Bostwick, D. G., Lieber, M. M., Thibodeau, S. N. and Jenkins, R. B. (1995) Frequent loss of heterozygosity at 7q31.1 in primary prostate cancer is associated with tumor aggressiveness and progression. *Cancer Res.,* 55:4114-4119; Elo, J. P., Harkonen, P., Kyllonen, A. P., Lukkarinen, O., Poutanen, M., Vihko, R. and Vihko, P. (1997) Loss of heterozygosity at 16q24.1-q24.2 is significantly associated with metastatic and aggressive behavior of prostate cancer. *Cancer Res.,* 57:3356-3359; Alers, J. C., Rochat, J., Krijtenburg, P. J., Hop, W. C., Kranse, R., Rosenberg, C., Tanke, H. J., Schroder, F. H. and van Dekken, H. (2000) Identification of genetic markers for prostatic cancer progression. *Lab Invest.,* 80:931-942; Alers, J. C., Krijtenburg, P. J., Vis, A. N., Hoedemaeker, R. F., Wildhagen, M. F., Hop, W. C., van Der Kwast, T. T., Schroder, F. H., Tanke, H. J. and van Dekken, H. (2001) Molecular cytogenetic analysis of prostatic adenocarcinomas from screening studies: early cancers may contain aggressive genetic features. *Am. J. Pathol.,* 158:399-406); however, very few genes have been identified to date. Amplifications on 11q13 have been reported in other cancers (Kusano, N., Okita, K., Shirahashi, H., Harada, T., Shiraishi, K., Oga, A., Kawauchi, S., Furuya, T. and Sasaki, K. (2002) Chromosomal imbalances detected by comparative genomic hybridization are associated with outcome of patients with hepatocellular carcinoma. *Cancer,* 94:746-751; Brookes, S., Lammie, G. A., Schuuring, E., de Boer, C., Michalides, R., Dickson, C. and Peters, G. (1993) Amplified region of chromosome band 11q13 in breast and squamous cell carcinomas encompasses three CpG islands telomeric of FGF3, including the expressed gene EMS 1. *Genes Chromosomes Cancer,* 6:222-231; Fantl, V., Richards, M. A., Smith, R., Lammie, G. A., Johnstone, G., Allen, D., Gregory, W., Peters, G., Dickson, C. and Barnes, D.

M. (1990) Gene amplification on chromosome band 11q13 and oestrogen receptor status in breast cancer. *Eur. J. Cancer,* 26:423-429; Lammie, G. A., Fantl, V., Smith, R., Schuuring, E., Brookes, S., Michalides, R., Dickson, C., Arnold, A. and Peters, G. (1991) D11S287, a putative oncogene on chromosome 11q13, is amplified and expressed in squamous cell and mammary carcinomas and linked to BCL-1. *Oncogene,* 6:439-444), but rarely in prostate cancer (Kasahara, K., Taguchi, T., Yamasaki, I., Kamada, M., Yuri, K. and Shuin, T. (2002) Detection of genetic alterations in advanced prostate cancer by comparative genomic hybridization. *Cancer Genet Cytogenet,* 137:59-63; El Gedaily, A., Bubendorf, L., Willi, N., Fu, W., Richter, J., Moch, H., Mihatsch, M. J., Sauter, G. and Gasser, T. C. (2001) Discovery of new DNA amplification loci in prostate cancer by comparative genomic hybridization. *Prostate,* 46:184-190). We have significantly narrowed the region on 11q13 identified by El Gedaily and Kasahara in advanced prostate cancer case (Kasahara, K., Taguchi, T., Yamasaki, I., Kamada, M., Yuri, K. and Shuin, T. (2002) Detection of genetic alterations in advanced prostate cancer by comparative genomic hybridization. *Cancer Genet Cytogenet,* 137:59-63; El Gedaily, A., Bubendorf, L., Willi, N., Fu, W., Richter, J., Moch, H., Mihatsch, M. J., Sauter, G. and Gasser, T. C. (2001) Discovery of new DNA amplification loci in prostate cancer by comparative genomic hybridization. *Prostate,* 46:184-190). In our intermediate and high risk of recurrence cohort, we identified a BAC clone mapping to 11q13.1 that showed a statistically significant increase in copy number in tumors from patients who failed following radical prostatectomy as compared to those who did not recur and that was an independent predictor of recurrence. MEN1 maps to this locus and recent prostate cancer gene expression profiling experiments identified elevated expression of MEN1 to be associated with recurrence (Lapointe, J., Li, C., Higgins, J. P., van de Rijn, M., Bair, E., Montgomery, M., Ferrari, M., Egevad, L., Rayford, W., Bergerheim, U. et al. (2004) Gene expression profiling identifies clinically relevant subtypes of prostate cancer. *Proc. Natl. Acad. Sci. U.S.A.,* 101:811-816). Our real-time expression analysis on RNAs from prostatectomy patients showed an increase in expression for MEN1 for several cases, all but one exhibited corresponding genomic gain for the 11q13 locus. The exception is interesting because it implies mechanisms independent of amplification can result in increased MEN1 expression in prostate cancer. There was no correlation between increased expression and stage or grade, possibly indicating that this marker acts independent of those clinical parameters.

Genes that have been implicated in pathways involving prostate cancer were also found to lie in regions of genomic gain and loss in this study. The oncogene MYC showed genomic gain in the progressors, and at an even higher frequency in the metastatic cohort, as compared to the non-progressors. The tumor suppressor RB1 was shown to be more frequently deleted in the progressors, and at an even a higher frequency in the metastatic tumors than the non-progressors. Apoptosis of prostate cancer cells wild type for Rb has been shown to occur by means of an intracellular pathway that involves the activation of Rb and repression of MYC transcription (Zhao, X. and Day, M. L. (2001) RB activation and repression of C-MYC transcription precede apoptosis of human prostate epithelial cells. *Urology,* 57:860-865). We observed that the combination of +8q24.21/−13q14.2 occurred in 40% of the metastases.

Recent work in the gene expression field reported that a subset of primary solid tumors share the gene expression signature of their corresponding organ metastases (Ramaswamy, S., Ross, K. N., Lander, E. S. and Golub, T. R. (2003) A molecular signature of metastasis in primary solid tumors. *Nat. Genet.,* 33:49-54). We propose that genomic changes in metastatic tumors can guide identification of the most important genomic changes in primary tumors. This should be especially useful in slow growing, highly heterogeneous tumors, such as prostate cancer. In addition, prostate cancer cells exhibit very heterogeneous genomic profiles. Metastatic prostate tumors that have evolved further and are more homogenous can help elucidate which genetic changes confer aggressive phenotypes in primary tumors. Pattern recognition analysis identified a combination of BAC clones that may be utilized as biomarkers for predicting metastasis at the time of biopsy or surgery, and therefore assist in the identification of patients who would benefit from the use of adjuvant therapy. For example, the BAC gained at 22q13.1 in FIG. 4 maps to platelet derived growth factor beta, PDGFB. This is intriguing since the receptors for PDGF have been shown to be expressed in advanced prostate cancer (Chott, A., Sun, Z., Morganstern, D., Pan, J., Li, T., Susani, M., Mosberger, I., Upton, M. P., Bubley, G. J. and Balk, S. P. (1999) Tyrosine kinases expressed in vivo by human prostate cancer bone marrow metastases and loss of the type 1 insulin-like growth factor receptor. *Am. J. Pathol.,* 155:1271-1279). The beta receptor in particular has recently been shown to serve as a recurrence predictor in a 5-gene model (Singh, D., Febbo, P. G., Ross, K., Jackson, D. G., Manola, J., Ladd, C., Tamayo, P., Renshaw, A. A., D'Amico, A. V., Richie, J. P. et al. (2002) Gene expression correlates of clinical prostate cancer behavior. *Cancer Cell,* 1:203-209). LIMK1 (LIM domain kinase 1), mapping to 7q11.23 in FIG. 4, has recently been shown to be overexpressed in prostate tumors and metastatic cell lines (Davila, M., Frost, A. R., Grizzle, W. E. and Chakrabarti, R. (2003) LIM kinase 1 is essential for the invasive growth of prostate epithelial cells: implications in prostate cancer. *J. Biol. Chem.,* 278:36868-36875). In the same report, partial reduction in LIMK1 was shown to abolish the metastatic invasiveness of prostate cells in vitro (Davila, M., Frost, A. R., Grizzle, W. E. and Chakrabarti, R. (2003) LIM kinase 1 is essential for the invasive growth of prostate epithelial cells: implications in prostate cancer. *J. Biol. Chem.,* 278:36868-36875). Additionally, the tumor suppressor PTEN maps to the BAC identified at 10q23.1 in the exploratory biomarker analysis shown in FIG. 4. Prostate-specific deletion of the murine Pten tumor suppressor gene has been shown to lead to metastatic prostate cancer (Wang, S., Gao, J., Lei, Q., Rozengurt, N., Pritchard, C., Jiao, J., Thomas, G. V., Li, G., Roy-Burman, P., Nelson, P. S. et al. (2003) Prostate-specific deletion of the murine Pten tumor suppressor gene leads to metastatic prostate cancer. *Cancer Cell,* 4:209-221).

A significant strength of aCGH is its ability to expeditiously and quantitatively map both copy number gains and single copy losses at multiple independent loci in clinical specimens. This study has significantly expanded the catalogue of recurrent aberrations found in prostate cancer and this may enable a deepened understanding of its etiology and progression. Amplification at 11q13.1 is predictive of post-operative disease recurrence, deletion at 8p23 is strongly associated with advanced disease stage and candidate genes have been identified at each locus and these may form the basis for future diagnostics and therapies pending independent clinical validation. Genomic profiles were obtained from organ metastases and used to interrogate the genomic profiles of primary tumors for genome aberrations associated with metastasis. This exploratory analysis yielded a large number (~40) of biomarkers that define metastatic genotypes.

Materials and Methods:

Patients

Prostatectomy patients were retrospectively selected from Erasmus University Medical Center in the Netherlands. The cohort consists of 64 prostate cancer patients who were either at intermediate or high risk of recurrence at diagnosis (D'Amico, A. V., Whittington, R., Malkowicz, S. B., Fondurulia, J., Chen, M. H., Kaplan, I., Beard, C. J., Tomaszewski, J. E., Renshaw, A. A., Wein, A. et al. (1999) Pretreatment nomogram for prostate-specific antigen recurrence after radical prostatectomy or external-beam radiation therapy for clinically localized prostate cancer. *J. Clin. Oncol.*, 17:168-172. Following surgery, PSAs were monitored every 3 months during the first year, bi-annually in the $2^{nd}$ year followed by yearly. 32 of these patients never had a biochemical failure after surgery (PSA<0.2 ng/ml) or any other evidence of disease recurrence. The median follow-up for the non-progressors was 11 years. The other 32 patients failed biochemically. In this study, a biochemical relapse was defined as a) two consecutive PSA serum levels$\geq$0.2 ng/ml with an interval of at least 3 months followed by an elevated PSA ($\geq$0.2 ng/ml), or b) a single observation of PSA>1 ng/ml followed by an elevated PSA ($\geq$0.2 ng/ml). PSA levels$\geq$0.2 ng/ml occurring in the first three months after radical prostatectomy were not considered a biochemical relapse if followed by undetectable (<0.1 ng/ml) PSA values. The progression-free survival was defined as the interval between the time of surgery and the first elevated PSA serum level ($\geq$0.2 ng/ml). Other clinical parameters, such as Gleason score, pathological stage, age at operation, pre-operative PSA and surgical margin status are listed in Table 1 for the 64 patients (32 progressors, 32 non-progressors).

TABLE 1

Clinical characteristics of the cohort

A. Progressors

| Patient | OperYr | AgeOper | PreOpPSA | Stage | Grade | ResMargin | ProgFree Survival | Progress Type |
|---|---|---|---|---|---|---|---|---|
| 1 | 1991 | 61 | 11.2 | 2a | 5 | 0 | 91 | PSA |
| 2 | 1992 | 63 | 23.6 | 2c | 7 | 0 | 73 | PSA |
| 3 | 1990 | 67 | 64.3 | 3c | 7 | 1 | 2 | M1b |
| 4 | 1994 | 61 | 23.7 | 4a | 7 | 1 | 26 | M1a |
| 5 | 1988 | 68 | 17.1 | 3c | 7 | 1 | 3 | PSA |
| 6 | 1991 | 71 | 29.6 | 4a | 7 | 0 | 44 | LR |
| 7 | 1994 | 72 | 7.1 | 2c | 7 | 1 | 23 | PSA |
| 8 | 1988 | 70 | 1 | 4a | 7 | 0 | 10 | LR |
| 9 | 1988 | 69 | 29 | 3c | 7 | 1 | 33 | M1b |
| 10 | 1993 | 65 | 11.8 | 3a | 7 | 0 | 52 | PSA |
| 11 | 1986 | 65 | No data | 3b | 7 | 1 | 38 | M1b |
| 12 | 1987 | 64 | No data | 3c | 7 | 1 | 83 | PSA |
| 13 | 1989 | 60 | 6.5 | 3a | 6 | 0 | 13 | PSA |
| 14 | 1989 | 65 | 5.5 | 3c | 7 | 1 | 37 | PSA |
| 15 | 1990 | 61 | 21 | 3b | 7 | 0 | 3 | LR |
| 16 | 1991 | 61 | 7.8 | 3a | 7 | 1 | 71 | LR |
| 17 | 1992 | 66 | 6.4 | 3a | 7 | 1 | 41 | PSA |
| 18 | 1992 | 70 | 25.1 | 4a | 7 | 0 | 1 | PSA |
| 19 | 1991 | 69 | 0.7 | 2a | 6 | 0 | 54 | LR + M1b |
| 20 | 1992 | 63 | 18.7 | 4a | 7 | 1 | 8 | LR + M1b |
| 21 | 1992 | 53 | 16.5 | 3a | 7 | 0 | 2 | LR + M1b |
| 22 | 1990 | 55 | 13.2 | 4a | 7 | 1 | 38 | LR |
| 23 | 1990 | 51 | 2.8 | 4a | 6 | 1 | 16 | PSA |
| 24 | 1992 | 58 | 108 | 4a | 5 | 0 | 5 | LR |
| 25 | 1992 | 47 | 11.5 | 3a | 7 | 0 | 2 | M1b + M1c |
| 26 | 1992 | 59 | 3.2 | 3a | 7 | 1 | 75 | M1b |
| 27 | 1989 | 59 | 16.9 | 4a | 7 | 0 | 13 | M1b |
| 28 | 1989 | 74 | 19.4 | 3a | 7 | 1 | 17 | PSA |
| 29 | 1990 | 65 | 25.2 | 3a | 7 | 1 | 83 | PSA |
| 30 | 1990 | 71 | 16.1 | 3a | 7 | 0 | 98 | PSA |
| 31 | 1991 | 69 | 17.8 | 4a | 7 | 0 | 4 | M1a + M1b + M1c |
| 32 | 1991 | 62 | 73.7 | 4a | 7 | 1 | 2 | LR + M1b |

B. Non-progressors

| Patient | OperYr | AgeOper | PreOpPSA | Stage | Grade | ResMargin |
|---|---|---|---|---|---|---|
| 33 | 1990 | 59 | 9.2 | 2b | 7 | 0 |
| 34 | 1990 | 64 | 7.4 | 2b | 6 | 0 |
| 35 | 1991 | 65 | 11.1 | 2c | 5 | 0 |
| 36 | 1989 | 60 | 19.4 | 3a | 7 | 0 |
| 37 | 1992 | 59 | 17.2 | 2c | 7 | 0 |
| 38 | 1992 | 51 | 16.1 | 2a | 7 | 1 |
| 39 | 1993 | 72 | 12.2 | 3b | 7 | 1 |
| 40 | 1994 | 66 | 9.7 | 2c | 6 | 1 |
| 41 | 1992 | 67 | 4.8 | 3a | 5 | 1 |
| 42 | 1993 | 52 | 2.2 | 3a | 7 | 0 |
| 43 | 1993 | 58 | 5.8 | 2c | 6 | 0 |
| 44 | 1987 | 59 | No data | 4a | 7 | 1 |
| 45 | 1993 | 67 | 2.2 | 2c | 6 | 0 |

TABLE 1-continued

Clinical characteristics of the cohort

| | | | | | | |
|---|---|---|---|---|---|---|
| 46 | 1994 | 65 | 10.6 | 2c | 6 | 0 |
| 47 | 1993 | 55 | 16.4 | 2c | 6 | 0 |
| 48 | 1994 | 62 | 21.5 | 2c | 6 | 0 |
| 49 | 1989 | 62 | 5.2 | 3b | 7 | 1 |
| 50 | 1990 | 59 | 18.6 | 3a | 7 | 0 |
| 51 | 1992 | 65 | 23.1 | 4a | 7 | 0 |
| 52 | 1992 | 67 | 2.2 | 3a | 6 | 0 |
| 53 | 1992 | 63 | 4.5 | 3a | 5 | 0 |
| 54 | 1991 | 49 | 21.8 | 3a | 6 | 0 |
| 55 | 1991 | 59 | 8 | 3a | 6 | 0 |
| 56 | 1991 | 70 | 11.7 | 2c | 7 | 0 |
| 57 | 1990 | 69 | 2.6 | 4a | 5 | 0 |
| 58 | 1990 | 61 | 2.5 | 4a | 5 | 0 |
| 59 | 1991 | 44 | 17.3 | 3a | 6 | 0 |
| 60 | 1991 | 68 | 13.5 | 3a | 6 | 0 |
| 61 | 1991 | 72 | 15.3 | 3a | 7 | 0 |
| 62 | 1991 | 51 | 7.5 | 3a | 7 | 1 |
| 63 | 1991 | 65 | 27.8 | 3b | 7 | 1 |
| 64 | 1991 | 52 | 5.6 | 3a | 7 | 0 |

Table 1 Legend:
OperYr = year of prostatectomy,
AgeOper = age of patient at time of surgery,
PreOpPSA = preoperative PSA,
Res Margin = resection margin status, 0 (negative) and 1 (positive),
ProgFreeSurvival = length of time (months) to biochemical relapse,
ProgressType = PSA = no data on local or distance recurrence,
LR = local recurrence,
M1a = metastasis in non-regional lymph node,
M1b = bone metastasis,
M1c = other site metastasis.
The Gleason Grading system (Gleason, D. F. (1992) Histologic grading of prostate cancer: a perspective. Human Pathology, 23: 273-279) and the TNM Classification (Hermanek, P., Hutter, R. V. P. and Sobin, L. H. (1997) TNM Atlas IUAC. 4th Ed ed. New York, Springer) were used. The usage of elevated (0.2 ng/ml or greater) PSA as a first indicator for imminent local or distant recurrent disease has been reported by several authors.

In order to study metastatic tumors, 15 hormone refractory, metastatic tumors from the Rapid Autopsy Program from the University of Michigan Prostate SPORE were evaluated (Rubin, M. A., Putzi, M., Mucci, N., Smith, D. C., Wojno, K., Korenchuk, S. and Pienta, K. J. (2000) Rapid ("warm") autopsy study for procurement of metastatic prostate cancer. Clin. Cancer Res., 6, 1038-1045). 15 tissue slices at 15 microns were extracted with a Wizard Genomic DNA Isolation kit (Promega, Madison, Wis.) according to the manufacturer's protocol. The DNA was further purified by phenol/chloroform extraction, followed by ethanol precipitation.

Tissue Processing

All paraffin-embedded formalin fixed prostate tissue blocks were stained with DAPI to outline tumor areas. A bore (1 mm-1 cm in diameter) attached to a microscope was used to punch a few millimeters deep into the selected tumor region. H & E's were performed for the first and the last slice corresponding to the punch to insure the tumor region was consistent from top to bottom.

DNA was extracted using the Puregene DNA isolation kit (Gentra Systems, Minneapolis, Minn.).

aCGH

The human version 2.0 BAC arrays were provided by the UCSF Array Core. Each array consists of 2460 BAC clones spotted in triplicate on chromium slides. The resolution is approximately 1.4 Mb. The aCGH protocol that was followed is detailed in our recent aCGH archived tissue technique paper (Paris, P. L., Albertson, D. G., Alers, J. C., Andaya, A., Carroll, P., Fridlyand, J., Jain, A. N., Kamkar, S., Kowbel, D., Krijtenburg, P. J. et al. (2003) High-resolution analysis of paraffin-embedded and formalin-fixed prostate tumors using comparative genomic hybridization to genomic microarrays. Am J Pathol, 162:763-770). Also included in this reference are details regarding the in-house imaging system and software that was used to process the arrays.

Table 2 displays the designations of the BACS used to probed the genomic locations. The table also includes genes identified in or near the BACs as well as sequence information for the BACs The BACs are generally available from Invitrogen, Inc. (Carlsbad, Calif.).

TABLE 2

| BAC Clone Name | Locus | Genes in or near BAC | Genbank accession numbers of DNA within BAC |
|---|---|---|---|
| GAINS | | | |
| CTB-172I13 | 2qte1 | | |
| RP11-1146E5 | 3q26.2 | EVI1 (AF487422) | AQ698393 |

TABLE 2-continued

| BAC Clone Name | Locus | Genes in or near BAC | Genbank accession numbers of DNA within BAC |
|---|---|---|---|
| RP11-114M1 | 3q26.32 | IRA1 | AC026355.13 |
| RP1-97B16 | 3q26.3 | PIK3CA (3q26.3) | STS RH70978 |
| RP11-88L18 | 5p15.1 | BASP1 | part of NT_006576, NT_023089 contig, ends of BAC at AQ281504, AQ281510, and AZ516846 |
| RP11-23D23 | 7p22.3 | GPR30; UNC84A; MAFK | part of NT_079592 contig, STS markers SHGC-32510 |
| CTC-329F6 | 7p22.3 | EIF3S9 | CL423016 (partial sequence) |
| RP1-117G9 | 7q11.23 | ELN (AK075494); LIMK1 (AK125511); WBSCR5; RFC2; CYLN2 | AK075494 (ELN) |
| RP11-96O16 | 7q11.22 | AUTS2 | part of NT_079593, NT_007758 contig, ends of BAC at: AQ313616 AQ313618 |
| RP11-213E22 | 7q22.1 | VGF, Serpine1, PLOD3, AP1S1 | Ends of BAC at: AQ484445 AQ484446 |
| CTD-2041G23 | 7q31.31 | CORTBP2 | End of BAC at AQ236419 |
| RP11-17O4 | 9q34.1 | ASB6 | part of NT_008470 contig, End of BAC at: B81878 |
| RP4-693L23 | 11p15.5 | p57 (KIP2) | WI-17359 (RH marker for KIP2) |
| RP5-1071I14 | 17q21.33 | NGFR | D17S797 |
| RP11-46E14 | 17q25.3 | CBX4; CBX8; GAA; DDX48 | part of NT_024871contig; Ends of BAC at: AQ201028 AQ201029 |
| RMC22P003 | 22q13.1 | PDGFB | D22S1108 |
| LOSSES | | | |
| RP11-253O5 | 4p13 | | part of NT_006238 contig End of BAC at: STS Markers SHGC4-344 |
| RP11-267K19 | 5q13.1 | PIK3R1 | part of NT_006431 contig End of BAC at: STS Markers AFMB281YB9 |
| RP11-135F5 | 5q14.3 | COX7C | part of NT_006713 contig. End of BAC at: AQ380700 |
| RP11-203J7 | 5q21.1 | PAM | part of NT_034772 contig End of BAC at: AQ419291 AQ419293 |
| RP11-115L24 | 5q21.2 | PAM | AC009815.2 End of BAC at: AQ348041 AQ348042 |
| CTD-2079J2 | 5q21.3 | FER | part of NT_034772 contig Ends of BAC at: STS Markers SGC31298 WI-13009 STSG39082 WI-6744 |
| RP11-73N22 | 5q23.1 | | CG734300, NT_034772 |
| RP11-217L13 | 6q14.1 | HMGN3 | NT_007299, AC027616, Ends of BAC at: STS Markers AFM191XA3 AFM191XA3 |
| RP11-28L24 | 6q21 | TUBE1; LAMA4 | part of NT_025741 contig Ends of BAC at: B87392 AQ003445 |

TABLE 2-continued

| BAC Clone Name | Locus | Genes in or near BAC | Genbank accession numbers of DNA within BAC |
|---|---|---|---|
| RP11-47E20 | 6q21 | BVES; POPDC3 | part of NT_025741 contig Ends of BAC at: AQ199394, AQ199397 |
| RP11-182G2 | 8p22 | TUSC3 | part of NT_030737 contig End of BAC at: STS Marker SHGC-1961 |
| RP11-76B12 | 8p21.2 | DOCK5 | part of NT_023666 contig End of BAC at: AQ281843 |
| RP11-232J22 | 8p21.2 | BNIP3L | part of NT_023666 contig End of BAC at: AQ485011 |
| CTD-2015D3 | 8p21.2 | ADRA1 | part of NT_023666 contig End of BAC at: B54151 B65002 AQ226511 AQ236188 |
| RP11-57I3 | 8p12 | NRG1 | part of NT_007995 contig End of BAC at: AQ082612, AQ115482 |
| RP11-129G17 | 10q23.31 | PTEN | AL353149.10 |
| RP11-14A4 | 13q14.11 | LHFP | part of NT_024524 contig End of BAC at: B81624 |
| CTD-2202J2 | 13q14.11 | FOX01A | End of BAC at: AQ151331 |
| RP11-17I11 | 13q14.11 | | part of NT_024524 contig Ends of BAC at: B82714 B82713 |
| RP11-217H23 | 13q14.13 | GTF2F2 | part of NT_024524 contig End of BAC at: STS Marker SHGC-11937 |
| CTD-2173J2 | 13q14.2 | RB1; CHC1L | part of NT_024524 contig Ends of BAC at: B94340, B94349 |
| RP1-269F22 | 13q14.3 | | D13S25 |
| RP11-12H11 | 16q23.1 | ADAMTS18 | part of NT_024797 contig. Ends of BAC at: B75800 B75801 |

Statistical Analysis

The tumor:reference fluorescence intensity ratios were converted to the $\log_2$ domain. The observed $\log_2$ratios were not included if there were fewer than two replicate spots (out of 3) or if the standard deviation of the replicates was above 0.2. Each array was normalized to have a median $\log_2$ratio of 0. The clones that were present in fewer than 75% of the samples (or 48 samples) were removed from the dataset (348 or 13% of the clones). 2127 clones remained in the dataset.

To identify the gained and lost clones in individual samples, we constructed sample-specific thresholds (Fridlyand, J., Snijders, A., Pinkel, D., Albertson, D. G. and Jain, A. N. (2004) Application of Hidden Markov Models to the analysis of the array CGH data. *Journal of Multivariate Analysis* (*Special Genomic Issue*), in press). The clones with $\log_2$ratios above or below +/−a tumor's threshold were considered gained or lost, respectively. To calculate thresholds, we used discrete-time Hidden Markov Model (Rabiner, L. R. (1989) A tutorial on hidden markov models and selected applications in sppech recognition. *Proc. IEEE*, 77, 257-286) to segment clones on individual chromosomes into the states corresponding to underlying copy numbers. The number of states was determined with the BIC (Schwarz, G. (1978) Estimating the dimension of a model. *The Annals of Statistics*, 6, 461-464) criterion. In order to increase robustness of the procedure, we used only those chromosomes that contained less than 3 different states and only those states that contained at least 20 clones. We assumed that experimental measurement error is independent of the underlying copy number. Thus, for each state and chromosome that met the above criteria, we calculated the median absolute deviation (MAD) of the $\log_2$ratios of the clones on that chromosome belonging to a given state. The final estimate of the standard deviation of the experimental noise, SD, was then calculated as the median of the above MAD values across all used states and chromosomes. Finally the thresholds were calculated conservatively as 2.5 times the SD for a given tumor. The ad-hoc justification for using this threshold lies in considering the standard normal distribution (1.2% of the standard normals are expected to exceed the absolute cut-off of 2.5). The frequency of gains and losses for a given clone in a group of interest was calculated as the proportion of samples in which a clone was gained or lost in that group.

We imputed the missing values (8.8% of the observations) using the K Nearest Neighbors (KNN) algorithm (Troyanskaya, O., Cantor, M., Sherlock, G., Brown, P., Hastie, T., Tibshirani, R., Botstein, D. and Altman, R. B. (2001) Missing value estimation methods for DNA microarrays. *Bioinformatics*, 17:520-525). We computed all pairwise correlations among the clones and assign 5 closest neighbors to each clone (i.e. the clones most highly correlated with a given clone). Then, if a particular clone was missing in a given sample, the missing value was replaced by the average of the values of that clone's 5 closest neighbors in that sample. To impute all missing values, we iterated the above procedure twice using 10 neighbors at the second iteration.

For a given phenotype, we looked for the clones with significantly different underlying copy number between the subtypes. Since the clones that rarely show an abnormal copy number are not a priori likely to contribute to the difference among subgroups, we reduce the multiplicity of the comparisons by only considering the clones that show the gain or loss separately in at least 20% of the samples. There were 122 such clones, with 35% located on chromosome 8 (almost all on 8p).

To test univariately for association between the copy number and a phenotype, for each clone we tested the null hypothesis that the distribution of the copy was the same in each of the subgroups, by using a t-statistic with pooled variance when two groups were being compared and F-statistic for more than two groups (Snedeckor, G. W. and G., C. W. (1989) In *Statistical Methods.* 5 ed. University Press, p. Chapter 5). The p-value for a clone was computed by considering the distribution of the t-statistic under the null hypothesis of no difference between the two groups. An adjustment for multiple comparisons was made so as to limit the probability of finding at least one false positive result. In practice, this was implemented using the maxT method (Westfall, P. H. and Young, S. S. (1993) *Resampling-based multiple testing: Examples and methods for p-value adjustment.* Wiley) by randomly permuting the subgroup labels, recomputing the statistic for each clone and recording the maximum absolute value of the statistic over all clones. We repeated the procedure 10,000 times. The observed statistic for a given clone was compared to the distribution of the recorded maxima and the adjusted p-value equal to the proportion of the recorded maximum values exceeding the absolute observed t-statistic for a given clone.

This patient sample was selected to have a 50% probability of recurrence. To determine independent predictors of recurrence, we fit the multivariate Cox-proportional hazards model using all of the clinical variables and the significant loci identified in the univariate analysis. All of the statistical analyses were done in the environment of the freely available statistical package R (Ihaka, R. and Gentleman, R. (1996) R: A language for Data Analysis and Graphics. *Journal of Computational and Graphical Statistics*, 5, 299-314).

We looked for BAC clones that could serve as a group to identify tumors with metastatic potential. The frequency of change for each BAC was computed and copy number aberrations that occurred in 20% or more of the progressors that later metastasized and organ metastases, but less than 20% of the non-progressors and vice versa were considered a differentiating BAC. For each clone the proportion of cases either above or below the defined threshold between non-progressors and those with metastases was compared using Fisher's one-sided exact test.

Validation of Candidate Genes with TaqMan

For validation of candidate genes, RNA was extracted from tumors and benign tissue obtained from 10 radical prostatectomy specimens and analyzed using TaqMan RNA quantitation. For each case, this was performed as follows. Twenty 13 micron slices were obtained from UCSF comprehensive Cancer Center fresh-frozen Tissue bank, with the first, tenth and twentieth sections H&E stained for evaluation of tissue types and amounts. Areas of interest on these slides were then marked to act as guides for microdissecting the areas for analysis from the remaining unstained sections; only areas with greater than 70% of the tissue of interest (benign prostate epithelium or tumor) were marked. The unstained slides were dehydrated using steps of 70%, 90% and 100% ethanol for one minute each followed by immersion in Xylene for 5 minutes. After the slides dried, outlined areas were microdissected from the slides using a scalpel blade, and the dissected tissue suspended into a lysis buffer containing 1% β-mercaptoethanol (RNeasy kit, Qiagen). The tissue was homogenized using a Qiashredder spin column (Qiagen) and the RNA extracted according to manufacturer's suggestions. The RNAs were run on an Agilent 2100 BioAnalyzer (Palo Alto, Calif.) to assess RNA quality. Tissue samples were retained in the study if there was not any significant RNA degradation.

TaqMan assays were carried out by the UCSF Genome Core. TaqMan primer-probe sets were available as Assays on Demand kits through ABI (Foster City, Calif.) for MAP4K2 and MEN1. The CSMD1 TaqMan primer-probe set was designed in-house and synthesized by IDT (Coralville, Iowa). The forward primer (5'-TTTCCAGATTTTTATC-CAAACTCTCTAA-3'; SEQ ID NO:1) and probe (5'-FAM-CACGTGGACCATTGAAGTGTCTCATGG-BHQ1-3'; SEQ ID NO:2) (BHQ=black hole quencher 1 from Biosearch Technologies, Novato, Calif.) lie within exon 19 and the reverse primer (5'-GTGTGAAAGATCATTTGAACTC-CTTT-3'; SEQ ID NO:3) spans exons 19 and 20 of CMSD1. Each tissue sample was run in triplicate. Good methodology was demonstrated by the standard deviation for the cycle threshold values of all three replicates being less than 0.3. The prostate tissue sample was retained in the study if the direction of change in expression for the candidate gene was the same compared to two reference genes (18S and GUS). Results are displayed as percentage of expression relative to GUS, since similar changes were seen for 18S.

Example 2

Risk assessment and counseling tools used to predict disease outcome in urology include nomograms and risk grouping models. Nomograms are scaled representations of statistical models defined by weighting significant predictors used to calculate the probability of a disease outcome. In contrast, risk grouping models use disease associated variables (e.g., prostate-specific antigen (PSA), Gleason grade, clinical stage) to assign outcome categories (e.g., high-risk, low-risk). Two of the most widely-used risk assessment tools currently available to predict biochemical failure after radical prostatectomy are a three-level categorization published by D'Amico et al. (D'Amico A V, Whittington R, Malkowicz S B, et al. *JAMA* 1998;280(11):969-74) and a continuous nomogram devised by Kattan et al. (Kattan M W, Eastham J A, Stapleton A M, Wheeler T M, Scardino P T. *J Natl Cancer Inst* 1998; 90(10):766-71). Nomograms have better predictive accuracy than some extant risk grouping models (Kattan M W, Zelefsky M J, Kupelian P A, Scardino P T, Fuks Z, Leibel S A. *J Clin Oncol* 2000;18(19):3352-9; Kattan M W, Heller G, Brennan M F. *Stat Med* 2003;22(22):3515-25) and are superior to expert assessment. The Kattan nomogram predicts outcome for higher risk patients better than other existing nomograms. These tools are convenient, useful for patient counseling and decision making, and applicable for use in clinical trials. However, the concordance rates for these nomograms and actual pathologic stage or recurrence approximate 68% (Ross P L, Scardino P T, Kattan M W. A catalog of prostate cancer nomograms. J Urol 2001;165(5): 1562-8). These instruments could be improved by adding phenotypic or genotypic markers as a component of assessment. Kattan et al.'s recent work incorporating IL6SR and TGFB into the preoperative nomogram for PSA recurrence after radical prostatectomy is the first to improve nomogram accuracy, to ~80%, with a new biomarker rather than biopsy data or a variation of PSA measurement (Kattan M W, Shariat S F, Andrews B, et al. *J Clin Oncol* 2003;21(19):3573-9). Glinsky et al. used gene expression profiling to stratify patients into risk groups for recurrence but does not report probability tables or nomograms based on this data (Glinsky G V, Glinskii A B, Stephenson A J, Hoffman R M, Gerald W L., *J Clin Invest* 2004;113(6):913-23). It should be noted that another report that used gene expression to predict outcome was a 5 gene model that included PDGFRβ, the receptor for a gene that maps to one of our GEMCaP biomarkers (Singh D, Febbo P G, Ross K, et al. *Cancer Cell* 2002;1(2):203-9).

It has been our hypothesis that genome copy number profiles can be used to assess risk of disease recurrence, metastasis, and for elucidation of the biological mechanisms of metastasis. To test our hypothesis, we have employed array comparative genomic hybridization (aCGH) to the analysis of multiple cohorts of prostate tumors. Array CGH is a powerful tool for biomarker discovery and identification of genes involved in CaP progression because it allows high resolution and quantitative detection of copy number aberrations in tumor genomes (Pinkel D, Segraves R, Sudar D, et al. *Nat Genet* 1998;20(2):207-11; Veltman J A, Fridlyand J, Pejavar S, et al. *Cancer Res* 2003;63(11):2872-80; Snijders A M, Nowee M E, Fridlyand J, et al. *Oncogene* 2003;22(27):4281-6) that can be associated with clinical outcome (Wilhelm M, Veltman J A, Olshen A B, et al. *Cancer Res* 2002;62(4):957-60). We have analyzed prostate tumors using aCGH from 64 men at intermediate to high-risk of progression with up to 16 years clinical follow-up (Paris P L, Andaya A, Fridlyand J, et al. *Hum Mol Genet* 2004;13(13):1303-13). Half of the patients progressed biochemically (PSA) and half did not. Included amongst the tumors that recurred are 12 primary tumors confirmed to have later metastasized to bone. In an independent study, the genomes of 15 organ metastases were analyzed using aCGH. Copy number profiles from the 12 primary tumors that metastasized and 15 metastases were used to detect signatures of metastasis in primary tumors. These events occur as relatively rare events in primary tumors but manifest as highly recurrent amplifications and deletions in the metastases. BAC clones at 39 loci (~2400 clones evaluated) were required to detect the signatures of metastasis (Paris P L, Andaya A, Fridlyand J, et al. *Hum Mol Genet* 2004;13(13):1303-13). We call these loci the genomic evaluators of metastatic CaP (GEMCap). This group of 39 BAC clones may be useful in predicting primary tumors that are poised for metastasis or have already seeded occult micrometastases. The ability of the 39 loci to predict postoperative recurrence was compared to the predictive value of the Kattan nomogram.

TABLE 3

GEMCaP and nomogram risk classification for 27 UCSF radical prostatectomy cases.

| Sample ID | Gleason sum | Margin status | Time to biochemical failure or secondary Tx or last PSA (months) | Biochemical or secondary Tx failure? | % aberrant GEMCaP loci | GEMCaP metastatic risk prediction | % of being disease free in 5 yr Kattan |
|---|---|---|---|---|---|---|---|
| 1 | 6 | negative | 38 | N | 0% | L | 80/89% |
| 2 | 6 | negative | 38 | N | 6% | L | 87% |
| 3 | 6 | negative | 26 | N | 11% | L | 89% |
| 4 | 6 | negative | 19 | N | 9% | L | N/A |
| 5 | 5 | positive | 36 | N | 5% | L | 77% |
| 6 | 7 | negative | 35 | N | 19% | L | 79% |
| 7 | 6 | negative | 36 | N | 3% | L | N/A |
| 8 | 6 | positive | 32 | N | 0% | L | 84% |
| 9 | 6 | negative | 23 | N | 6% | L | 91% |
| 10 | 7 | negative | 31 | N | 11% | L | 80% |
| 11 | 8 | negative | 30 | N | 20% | L | 82% |
| 12 | 6 | negative | 9 | N | 6% | L | 89% |
| 13 | 9 | negative | 21 | N | 14% | L | 84% |
| 14 | 9 | negative | 19 | N | 0% | L | 55% |
| 15 | 9 | positive | 5 | Y | 29% | H | 64% |
| 16 | 6 | positive | 10 | Y | 31% | H | 91% |
| 17 | 9 | positive | 25 | Y | 56% | H | 77% |
| 18 | 7 | negative | 3 | Y | 25% | H | 70% |
| 19 | 9 | negative | 4 | Y | 24% | H | 76% |
| 20 | 7 | negative | 16 | Y | 41% | H | 71% |
| 21 | 7 | positive | 11 | Y | 22% | H | 73% |
| 22 | 7 | positive | 13 | Y | 8% | L | 35% |
| 23 | 8 | positive | 1 | Y | 8% | L | 76% |
| 24 | 9 | positive | 7 | Y | 9% | L | 53% |

TABLE 3-continued

GEMCaP and nomogram risk classification for 27 UCSF radical prostatectomy cases.

| Sample ID | Gleason sum | Margin status | Time to biochemical failure or secondary Tx or last PSA (months) | Biochemical or secondary Tx failure? | % aberrant GEMCaP loci | GEMCaP metastatic risk prediction | % of being disease free in 5 yr Kattan |
|---|---|---|---|---|---|---|---|
| 25 | 9 | negative | 43 | N | 27% | H | 73% |
| 26 | 7 | negative | 35 | N | 28% | H | 59% |
| 27 | 9 | negative | 7 | N | 31% | H | N/A |

TABLE 4

Comparing GEMCaP and Kattan nomogram with biochemical recurrence.

|  | GEMCaP | Kattan |
|---|---|---|
| Accuracy | 78% | 80% 75% |
| (+) Predictive Value | 70% | 64% |
| (−) Predictive Value | 82% | 90% |

Methods

Patient Selection and Tissue Processing: aCGH was available for 27 UCSF radical prostatectomy patients that were selected based on Gleason grade for a separate study. Ten 13 micron slices were cut for each case from fresh frozen prostate tissue blocks. H & E's were performed on 5 micron slices representative of the beginning and the end of the cut section. A single pathologist (J.S.) outlined areas of greater than 80% tumor for microdissection with a scalpel. DNA was extracted using a proteinase K digestion and the Promega Wizard Kit (Madison, Wis.) as per the manufacturer's instructions. Two phenol:chloroform extractions followed by an ethanol precipitation were performed after the Promega kit's final elution step.

aCGH: The human version 2.0 BAC arrays were purchased from the UCSF Array Core. Each array consists of 2,460 BAC clones spotted in triplicate on chromium slides (Pinkel D, Segraves R, Sudar D, et al. *Nat Genet* 1998;20(2):207-11). The resolution is approximately 1.4 Mb. We followed our published hybridization protocol (Paris P L, Albertson D G, Alers J C, et al. *Am J Pathol* 2003;162(3):763-70).

aCGH Statistical Analysis: The tumor:reference fluorescence intensity ratios were converted to the log2 domain and the replicate spots were averaged. The observed log2ratios were not included if there were fewer than two replicate spots (out of 3) or if the standard deviation of the replicates was greater than 0.2. Each array was normalized to have a median log2ratio of 0. To identify the gained and lost clones in individual samples, sample-specific thresholds were constructed. The GEMCaP clones with log2ratios above or below +/− a tumor's threshold were considered gained or lost, respectively. An Excel Macro has been written in our laboratory to determine the percentage of aberrant GEMCAP loci based on the inputted aCGH data and TBT for a given patient. All tumors were analyzed with this Macro.

Methods of Analysis for GEMCaP and Nomograms: As a summary measure, if more than 20% of the GEMCaP loci were aberrant for an individual patient, then this was defined as a high metastatic risk case. Patients were also classified according to the Kattan preoperative nomogram ((Kattan M W, Eastham J A, Stapleton A M, Wheeler T M, Scardino P T. *J Natl Cancer Inst* 1998;90(10):766-71), http://www.mskcc.org/mskcc/html/10088.cfm) which weights the preoperative PSA, biopsy Gleason grade and clinical T stage into a summary predictive 5 year probability of remaining recurrence free.

Results

Preliminary GEMCaP Biomarker Evaluation

To evaluate the predictive strength of the GEMCaP loci we asked if we could blindly sort in silico 27 primary prostate tumors into metastasis risk groups (low, high) based solely on the copy number status of these 39 markers. The twenty-seven radical prostatectomy cases consisted of low, intermediate and high-grade tumors. Using the Gleason categorization suggested by Steinberg et al., 10 tumors were low-grade (Gleason Score≦6), 7 were intermediate grade (Gleason Score=7) and 10 were high-grade (Gleason Score≧8) (Steinberg D M, Sauvageot J, Piantadosi S, Epstein J I. *Am J Surg Pathol* 1997;21(5):566-76). Follow-up data was available for all patients. The test set consisted of 17 non-progressors (median follow-up=31 months) and 10 progressors. A progressor was defined as a patient with a PSA≧0.2 ng/ml on 2 consecutive occasions following prostatectomy, and/or a second cancer treatment for evidence of metastases ≧6 months after surgery. A tumor with 20% or less of the GEMCaP loci aberrant was classified as low-risk of metastasis, and greater than 20% was classified as high-risk of metastasis. The biomarker group alone could predict risk of recurrence with an accuracy of 78% (21/27, Table 3).

Accuracy of GEMCaP Biomarkers and Nomograms

The Kattan nomogram was used to analyze the 27 UCSF patients for whom GEMCaP predictions had been performed. Both predictions were made independent of one another and in a blinded fashion as to outcome status. The results are shown in Table 3. There were cases where both methods (i.e. GEMCAP and nomogram) seemed comparable in predicting risk. For example, patient #5 was at low-risk of failure using the GEMCAP loci, however he was at moderate risk of recurrence according to the nomogram. To date, patient #5 has not experienced a recurrence after 3 years of follow-up. Conversely, patient #22 who recurred following surgery was at high-risk according to the nomogram, but not the GEMCAP loci. This preliminary study shows that there are patients who could benefit from the apparent complementary nature of these two methods.

For this pilot sample with 60% of the patients remaining disease free for the observed duration of this study, the accuracy of the composite GEMCaP loci classification was 78% compared with 75% by applying the Kattan nomogram to identify being at least 80% recurrence free at 5 years (Table 4). The positive predictive values for detecting recurrence were 70% and 64%, respectively. The negative predictive values for remaining recurrence-free were 82% and 90%, respectively. These results suggest a strong ability of the GEMCAP loci to accurately identify patients at risk of recurrence.

Discussion

Our 78% accuracy in predicting recurrence with BAC-based biomarkers compared to 75% with a nomogram is extremely encouraging. In 3 of the 6 samples where the biomarker group did not accurately assess recurrence, each had positive surgical margins suggesting that these patients may have failed for reasons independent of genetics. For the remaining three samples (Table 3: #25-#27), one has been followed for less than four years, one less than three years, and one less than a year. We suggest that these types of patients could be considered candidates for immediate adjuvant therapy or at minimum, more active surveillance (Zincke H, Lau W, Bergstralh E, Blute M L. *J Urol* 2001;166(6):2208-15).

GEMCaP is a good tool for prognosis prediction and treatment selection for prostate cancer patients. For example, in this preliminary test set there were 3 negative margin cases (Table 3: #18-#20) who recurred. The traditional method of predicting disease course using a nomogram predicts that these individuals have a fairly high probability of being disease free for five years (60-81%) following radical prostatectomy. However, our GEMCAP analysis predicted all three were at high-risk of a postoperative recurrence. It is noteworthy that the three recurrences occurred within 16 months of surgery suggesting that GEMCaP analysis might potentially be useful for identifying patients with genetically aggressive disease and therefore good candidates for immediate adjuvant, systemic therapy.

An advantage to this approach is that DNA is a stable molecule and aCGH is quantitative. Overall accuracy of nomograms ranges from 50-70% and this might ultimately be increased by inclusion of the GEMCAP loci. Identification of patients at risk for progression will assist clinicians in tailoring appropriate follow-up schedules and adjuvant therapy decisions.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for determining the risk of metastasis of prostate cancer in a human who has or had prostate cancer, the method comprising, detecting in a prostate tumor sample from the human the number of copies per cell of each of the genomic regions: 2qtel, 3q26.2, 3q26.32, 5p15.1, 7p22.3, 7q11.23, 7q11.22, 7q22.1, 7q31.31, 9q34.11, 11p15.5, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14 and 16q23.1, wherein an increase in the number of copies per cell of each of the genomic regions: 2qtel, 3q26.2, 3q26.32, 5p15.1, 7p22.3, 7q11.23, 7q11.22, 7q22.1, 7q31.31, 9q34.11, 11p15.5, 17q21.33, 17q25.3 and 22q13.1 and/or a decrease in the number of copies per cell of each of the genomic regions: 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14 and 16q23.1, compared to the number of copies per cell in non-cancer cells, indicates an increased risk of prostate cancer metastasis.

2. The method of claim 1, wherein said detecting comprises hybridizing genomic DNA present in the prostate tumor sample with at least one BAC selected from the group consisting of CTB-172I13, RP11-1146E5, RP11-114M1, RP1-97B16, RP11-88L18, RP11-23D23, CTC-329F6, RP1-117G9, RP11-96016, RP11-213E22, CTD-2041 G23, RP11-1704, RP4-693L23, RP5-1071114, RP11-46E14, RMC22P003, RP11-25305, RP11-267K19, RP11-135F5, RP11-203J7, RP11-115L24, CTD-2079J2, RP11-73N22, RP11-217L13, RP11-28L24, RP11-47E20, RP11-182G2, RP11-76B12, RP11-232J22, CTD-2015D3, RP11-5713, RP11-129G17, RP11-14A4, CTD-2202J2, RP11-17I11, RP11-217H23, CTD-2173J2, RP1-269F22, and RP11-12H11.

3. The method of claim 1, wherein said genomic regions comprise the genes EVI1, PIK3CA, EIF3S9, ELN, AUTS2, VGF, Serpinel, PLOD3, AP1S1, CORTBP2, p57 (KIP2), NGFR, CBX4, CBX8, PDGFB, FER, TUBE1, LAMA4, BVES, POPDC3, TUSC3, DOCK5, BNIP3L, ADRA1, NRG1, LHFP, GTF2F2, RB 1 and CHC1L.

* * * * *